United States Patent [19]
Payrat et al.

[11] Patent Number: 5,614,106
[45] Date of Patent: Mar. 25, 1997

[54] METHOD AND APPARATUS FOR COLLECTION OF PLATELETS

[75] Inventors: Jean M. Payrat, Nivelles, Belgium; Donald W. Schoendorfer, Santa Ana, Calif.

[73] Assignee: Baxter International Inc., Deerfield, Ill.

[21] Appl. No.: 459,529

[22] Filed: Jun. 2, 1995

Related U.S. Application Data

[63] Continuation of Ser. No. 30,710, Mar. 12, 1993, abandoned.

[51] Int. Cl.$^6$ .......................... B01D 37/00; B01D 36/00; B01D 21/26

[52] U.S. Cl. .................. 210/767; 210/206; 210/257.1; 210/782; 210/789; 210/800; 210/805

[58] Field of Search .................. 210/650, 767, 210/696, 698, 782, 789, 805, 206, 252, 257.1, 321.67, 800, 321.68, 295, 435, 456, 418; 604/4, 5, 6; 252/1; 435/2

[56] References Cited

U.S. PATENT DOCUMENTS

| | | | |
|---|---|---|---|
| 4,713,176 | 12/1987 | Schoendorfer et al. | 210/645 |
| 4,776,964 | 10/1988 | Schoendorfer et al. | 210/782 |
| 4,851,126 | 7/1989 | Schoendorfer | 210/651 |
| 4,857,508 | 8/1989 | Adams et al. | 514/18 |
| 4,911,833 | 3/1990 | Schoendorfer et al. | 210/782 |
| 4,925,665 | 5/1990 | Murphy | 435/2 |
| 5,135,667 | 8/1992 | Schoendorfer | 210/782 |
| 5,171,456 | 12/1992 | Hwang et al. | 210/782 |

FOREIGN PATENT DOCUMENTS

WO91/19554 12/1991 WIPO.

OTHER PUBLICATIONS

Hester, et al., "Anticoagulation in Donor Hemapheresis," *Donor Hemapheresis*, 1989, pp. 41–47.
Aster, "The Anticoagulants of Choice for Platelet Tranfusions," *Transfusion*, 1966, pp. 32–38.
Chappell, "Platelet Concentrates from Acidified Plasma: A Method of Preparation Without the Use of Additives," *Transfusion*, 1966, pp. 308–309.
Mathias et al., Evaluation of Plasma Collected with Five Different Standard Anticoagulant. Solutions using a "Spinning Membrance Device," *Transfusion Science*, 1990, pp. 205–210.
Rock et al. "Plasma Collection Using an Automated Membrane Device," *Transfusion*, vol. 26, No. 3, pp. 269–271, (May–Jun. 1986).
Autopheresis C® Plasmapheresis System brochure (1987).

*Primary Examiner*—John Kim
*Attorney, Agent, or Firm*—Andrew G. Kolomayets; Joseph B. Barrett; Bradford R. L. Price

[57] ABSTRACT

Methods and apparatus are disclosed for separating and collecting blood fractions or components such as platelets. A first anticoagulant solution is added to whole blood, which is then separated into platelet-rich plasma and red cells. A second anticoagulant is added to the platelet rich plasma, which is then separated into platelet-poor plasma and platelet concentrate. The rate of red cell sedimentation is increased and the time of the separation/collection procedure may be reduced when the pH of the first anticoagulant is greater than approximately 6.0.

43 Claims, 10 Drawing Sheets

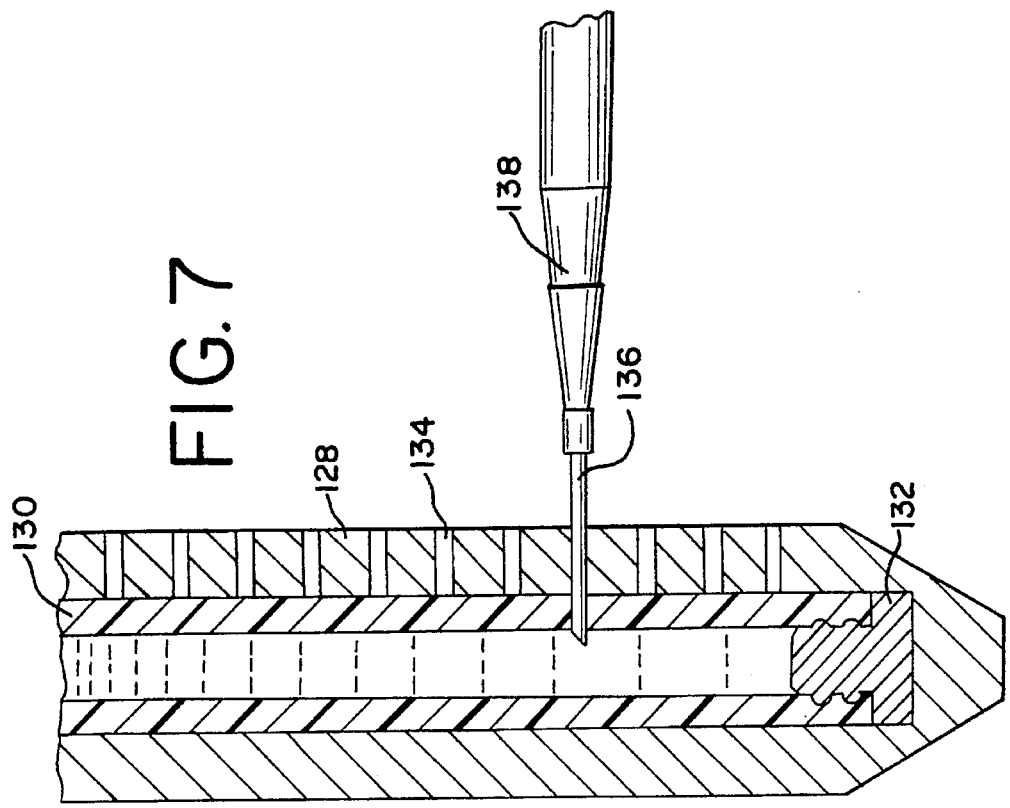
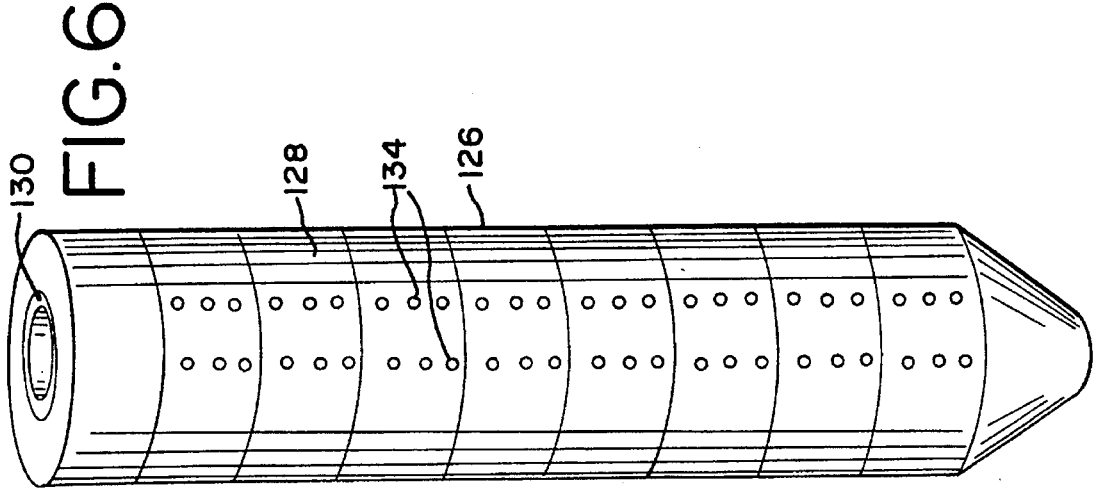

METHOD AND APPARATUS FOR COLLECTION OF PLATELETS

This is a continuation of application Ser. No. 08/030,710 filed on Mar. 12, 1993, now abandoned.

BACKGROUND OF THE INVENTION

The present invention relates generally to blood apheresis and, more specifically, to a method and apparatus for more efficient separation and collection of blood components, specifically, blood platelets.

Apheresis or hemapheresis generally refers to the separation of blood or blood components into further components or fractions such as red cells, white cells, platelets and plasma. In typical apheresis procedures, whole blood is collected from a donor or patient, anticoagulant is added to the whole blood, and the anticoagulated whole blood is then separated into two or more desired components or fractions.

The separated components may be collected from a healthy donor for later administration to a patient. This is sometimes referred to as "donor apheresis". One of the most common donor apheresis procedures is plateletpheresis or platelet apheresis. In plateletpheresis, platelets are collected from a healthy donor. The collected platelets are then administered to, for example, cancer patients whose ability to generate platelets from their own bone marrow has been impaired by chemotherapy.

Alternatively, the separated components may be removed as part of the treatment of a patient. This is sometimes referred to as "therapeutic apheresis". One such therapeutic apheresis procedure is plasmapheresis. In plasmapheresis, plasma carrying a disease or other undesired substances is removed from a patient and replaced with normal plasma or other replacement fluid. Other types of therapeutic apheresis procedures include removal of white blood cells or platelets from patients with excess amounts of those components.

Currently, there are several commercially available hemapheresis systems for separating blood or blood components into further components or fractions. One such system is the Autopheresis-C® system sold by Baxter Healthcare Corporation of Deerfield, Ill. The Autopheresis-C® system includes a microprocessor-controlled instrument and a disposable tubing set attached to the instrument. The disposable tubing set comprises two portions that are integrally connected to each other. The Autopheresis-C® system may be used for various donor or therapeutic apheresis procedures, including plateletpheresis.

Typically, the collection of platelets using the Autopheresis-C® system proceeds in two stages or phases, as disclosed in U.S. Pat. No. 4,851,126 entitled "Apparatus and Methods for Generating Platelet Concentrate" which is incorporated by reference herein. In the first stage of the two stage system, the instrument and one portion of the tubing set are used to collect platelet-containing plasma often called platelet-rich plasma (PRP). During the first stage, whole blood is withdrawn from a donor and combined with an anticoagulant solution. The anticoagulated whole blood is introduced into a separation chamber, where it is separated into red blood cells and PRP. The red cells are returned to the donor and the PRP is collected in a container. After a sufficient volume of PRP has been collected in the container, the instrument and tubing set are disconnected from the donor, who is then free to leave.

After the first stage is completed, the portion of the tubing set used during the first stage is disconnected from the instrument and is replaced with the portion of the disposable tubing set used for the second stage of the procedure. During the second stage, the PRP that was collected in the first stage is introduced into a separation chamber where platelets are separated from plasma to provide platelet-poor plasma (PPP) and platelet concentrate. The platelet concentrate is directed to a plastic container, while the PPP is collected in a separate collection bag.

Another automated system for separating blood or blood components into fractions or further components is the CS-3000® Cell Separator, also sold by Baxter Healthcare Corporation. The CS-3000® Separator also includes a microprocessor controlled instrument and a presterilized, disposable tubing set attached to the instrument.

In a CS-3000® platelet procedure, whole blood is withdrawn from a donor and is mixed with an anticoagulant solution. The anticoagulated whole blood is introduced into a separation chamber where it is centrifugally separated into packed red cells and PRP. As whole blood continues to enter the separation chamber, the separated red cells and PRP exit the chamber. The red cells are returned to the donor while the PRP enters a second separation/collection chamber, where the PRP is separated into platelet concentrate and platelet-poor plasma (PPP). The PPP is removed from this chamber and is returned to the donor, leaving only the platelet concentrate in the separation/collection chamber.

With the advent of chemotherapy as a method of cancer treatment, the demand for platelets collected from healthy donors has grown considerably. In order to meet this demand, hospitals and other platelet collection centers must rely on the good will of volunteer donors willing to take the time to donate platelets. Accordingly, efforts are made to make platelet collection procedures as quick and easy as possible with minimal inconvenience to the donor. For this reason, it is the desire of those in the field of blood apheresis to provide methods and apparatus capable of collecting the maximum number of platelets from a given donor in as short a time as possible, while also reducing the risk of any adverse donor reactions during the procedure.

Increasing the platelet yield from a given donor also has certain medical benefits. For example, a platelet dose collected from a single donor is more desirable than a platelet dose that has been pooled from several random donors, because it does not expose the patient or platelet recipient to the blood of several individuals. Administering platelets from a single donor also allows the patient to identify specific donors and reduces the risk of "alloimmunization", a condition in which a patient will no longer respond to platelet transfusions.

Shorter collection times are desirable because they are less of a burden on the donor. From an administrative standpoint, reducing the collection time also allows for more platelet collection procedures to be scheduled and performed.

In addition, because of laboratory testing that must be conducted on the collected platelets and schedules of donors and patients that must be coordinated, several days may pass between the platelet collection from the donor and the platelet transfusion into the patient. Accordingly, it is necessary that the viability of the collected platelet product be maintained for an extended period of time. In the case of platelets, it is preferred that the collected platelets be capable of long-term storage (i.e. at least five (5) days).

The viability of platelets during storage is a function of several variables such as pH of the concentrate, the availability of nutrients, oxygen transmission through the storage container, etc. as is well known in the field. Typically, the initial pH and the nutrients, such as dextrose, are provided by the anticoagulant added to the whole blood at the beginning of the procedure.

In addition to the nutrients, the anticoagulant typically contains citrate. Citrate aids in (a) preventing blood from clotting as it travels through the tubing, (b) preventing blood from clotting as it is separated and (c) preventing platelets from clumping during storage. Although citrate can be metabolized by humans, too much citrate can cause adverse reactions, with symptoms such as chills and tingling in the fingers and around the mouth. Of course, during typical blood apheresis procedures, a quantity of citrate is contained with the red cells when they are returned to the donor or patient. If too much anticoagulant is added to whole blood during the apheresis procedure, the donor or patient may experience the "citrate reaction" described above. For this reason, it is important to control and preferably reduce the amount of anticoagulant added to the whole blood during an apheresis procedure.

Recently, systems and methods have been developed whereby platelet yield can be improved while reducing the amount of anticoagulant administered to the donor. U.S. Pat. No. 5,135,667 to Schoendorfer (which is incorporated by reference herein), describes a method and apparatus for improving platelet yield by adding selected (and reduced) amounts of anticoagulant solution Acid-Citrate-Dextrose-A (ACD-A) at different times during a platelet collection procedure. Schoendorfer utilized a single anticoagulant container from which a selected (and reduced) amount of anticoagulant ACD-A was added to the whole blood during the first stage of a platelet procedure on the Autopheresis C® system described above. After a preselected amount of platelet-rich plasma had been collected during the first stage of the procedure, additional ACD-A was then added to the platelet-rich plasma to prevent the platelets from coagulating during the separation of the PRP into platelet concentrate and PPP, and also to provide a sufficient amount of anticoagulant and nutrients so that the platelet concentrate may be stored for at least 5 days.

Specifically, Schoendorfer disclosed that reducing the amount of anticoagulant ACD-A added to whole blood (during the first stage of the procedure) from the previously accepted standard of 8% ACD-A to 6% or less ACD-A (per total anticoagulated whole blood volume) significantly improved the platelet collection efficiency and the platelet yield. Adding less anticoagulant to the whole blood and, as a result, less citrate to the whole blood had the additional benefit of reducing the amount of citrate returned to the donor with the red cells, thereby reducing the possibility of citrate reactions in the donor or patient.

Schoendorfer attributed a portion of the increase in platelet yield to less fluid volume dilution due to less anticoagulant. However, Schoendorfer could not explain the other portion of the increase in platelet yield. Moreover, Schoendorfer did not report any effect on the collection time.

SUMMARY OF INVENTION

As a result of the present invention, a fuller understanding of the phenomenon observed by Schoendorfer is obtained and novel methods and apparatus for improved blood apheresis and improved platelet collection in particular may be provided.

More specifically, in accordance with the present invention, a new method is provided for collecting and storing blood platelets. The method includes providing a quantity of whole blood and adding a first anticoagulant to the whole blood. The platelets are then separated from the whole blood and, unlike prior platelet collection procedures, a second and different anticoagulant is added to the platelets. As a result, the first anticoagulant may be chosen to enhance the separation of platelets from other blood components and reduce donor reactions to citrate, and the second anticoagulant may be chosen to enhance platelet viability during storage.

In accordance with other aspects of the present invention, a system for separating platelets from whole blood may be provided wherein the system includes a separation chamber for separating platelets from whole blood and means defining an upstream flow path communicating with the separation chamber. The upstream flow path includes a whole blood source for providing whole blood to the separation chamber and means for introducing a first anticoagulant into the upstream flow path from a source of anticoagulant. The system further includes means defining a downstream flow path communicating with the separation chamber and means for transporting platelets from the separation chamber. Finally, the system includes means for introducing a second and different anticoagulant solution to the downstream flow path or the separation chamber.

Further in accordance with the present invention, a method for collecting blood platelets is provided. The method includes providing a quantity of whole blood, adding a selected amount of an anticoagulant to the whole blood wherein the anticoagulant has a pH greater than 6.0 and then separating the platelets or plasma from the whole blood.

These and other aspects of the present invention are described in detail in the following description of the attached drawings and the preferred embodiment of the present invention.

BRIEF DESCRIPTION OF THE DRAWINGS

FIGS. 6 and 7 show the centrifugation apparatus used to evaluate the composition of blood anticoagulated with different anticoagulant solutions;

DETAILED DESCRIPTION OF THE DRAWINGS

Figure 1:
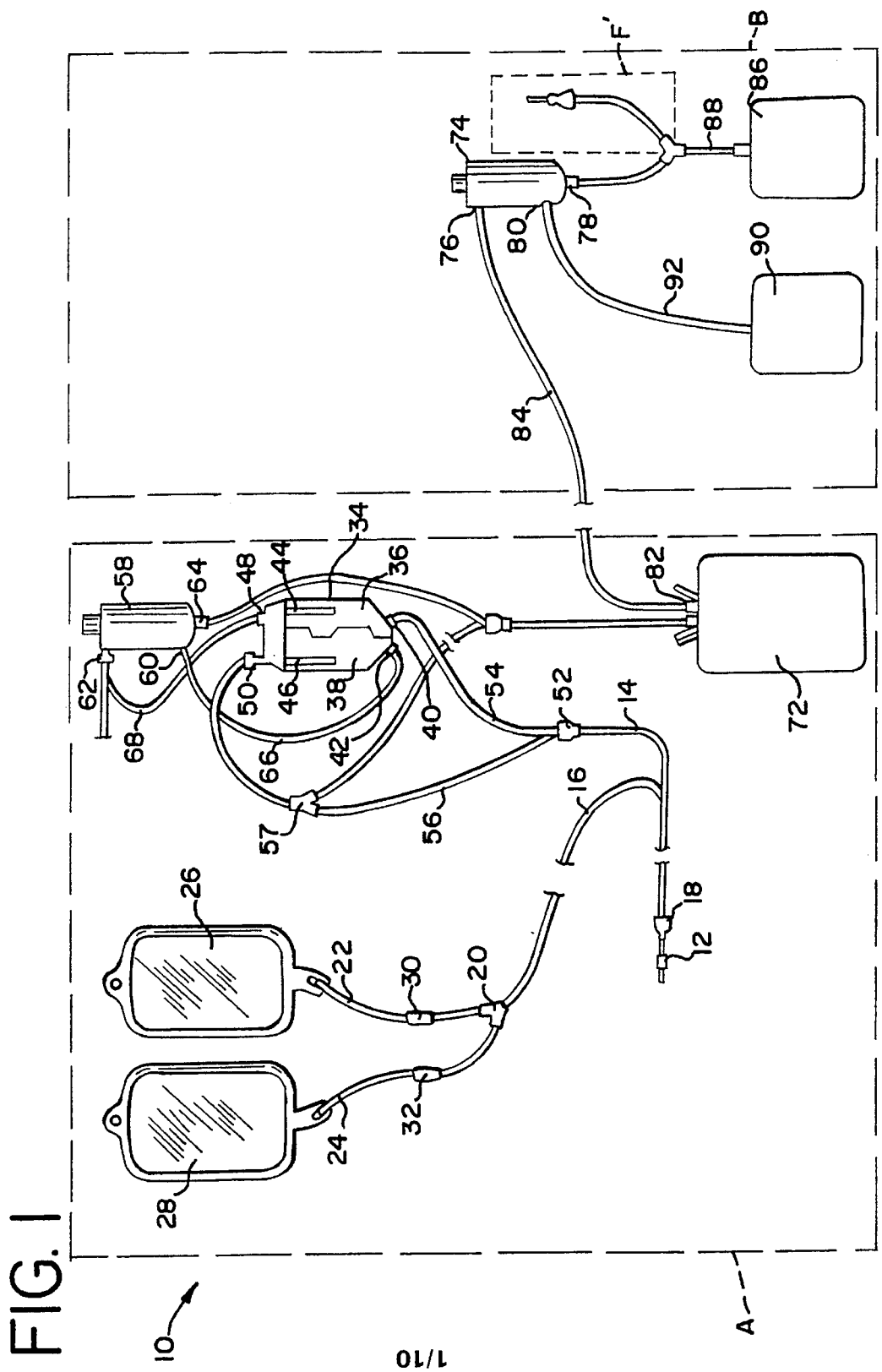
FIG. 1 is a plan view of the first and second portions of a tubing/separator set embodying the present invention, wherein the set includes two pre-attached anticoagulant containers with different anticoagulants in each container.

Referring now to FIG. 1 of the drawings, one aspect of the present invention is generally embodied in an integral presterilized disposable separation tubing set. The tubing set 10 includes a phlebotomy needle 12 for alternately receiving whole blood from and returning one or more blood fractions, such as packed red cells, to the donor. Phlebotomy needle 12 communicates with blood line 14. One end of an anticoagulant line 16 joins blood line 14 at connection site 18. The opposite end of anticoagulant line 16 includes a Y-connector 20 with branch lines 22 and 24 extending therefrom. Lines 22 and 24 are attached to containers of anticoagulant 26 and 28, respectively. In the preferred embodiment, containers 26 and 28 may be preattached to lines 22 and 24, thus forming part of the set 10. Alternatively, containers 26 and 28 may be provided separately and attached to set 10 by utilizing typical piercing spikes (not shown) at the ends of lines 22 and 24, as is well known in the medical field. Fluid flow through lines 22 and 24 may be manually controlled by roller clamps 30 and 32 or, alternatively, may be automatically controlled by the apheresis instrument.

The set 10 also includes a reservoir 34. The reservoir 34 is divided into a pair of side-by-side compartments 36, 38. Ports 40 and 42 are provided at the lower ends of the compartments 36, 38, respectively. Mesh screen/filter tubes 44, 46 are disposed in compartments 36, 38, respectively, in communication with respective inlet ports 48 and 50 at the upper end of the reservoir 34. Blood line 14 branches, at a Y-connection 52, into branch line 54 connecting the blood line 14 with the port 40 of compartment 36, and a branch line 56 which connects the blood line 14 with the port 50 of compartment 38. The set 10 additionally includes a separator 58 for separating platelet-rich plasma and packed red cells from anticoagulated whole blood. A separator of this type is described and illustrated in PCT International Publication WO 88/05332, as well as in U.S. Pat. No. 4,776,964, Schoendorfer et al., entitled "Closed Hemapheresis System and Method," which are incorporated by reference herein. For present purposes, separator 58 has a whole blood inlet port 60, a packed cell outlet port 62 and a platelet-rich plasma (PRP) outlet port 64. The line 66 connects the lower whole blood outlet port 42 of the reservoir compartment 38 with the inlet port 60 of separator 58. A line 68 connects the packed cell outlet port 62 of the separator 58 with the inlet port 48 for supplying packed cells to the compartment 36 of the reservoir 34. Tubing 70 connects the platelet-rich plasma outlet port 64 of the separator 58 with a platelet-rich plasma (PRP) collection container 72.

The foregoing described portion of the set 10 is, for convenience hereinafter, identified as the first stage portion of set 10, identified as "A" in FIG. 1. The remaining portion of the set 10, the second stage set portion, is identified as "B" in FIG. 1. The area labelled "B'" (B prime) in FIG. 1 illustrates an alternative embodiment having a second, return needle to the donor. It will be appreciated from this description that the first and second stage portions A and B form an integral or unitary set 10 which is packaged and sold for one-time use with the instrument disclosed in FIGS. 2 and 3 hereof.

PRP container 72 serves as the source of platelet-rich plasma for the second stage procedure. After installation of the second stage portion B of set 10 on the instrument referred to generally by the letter "H", the PRP in container 72 is separated into platelet poor plasma (PPP) and platelet concentrate. The second stage portion may also include a separator 74 of the rotary filter membrane type, such as described and illustrated in Canadian Pat. No. 1,261,765. For present purposes, the separator 74 filters the platelet-rich plasma received from container 72 to provide platelet concentrate and depleted or platelet-poor plasma filtrate (PPP). The separator 74 has a platelet-rich plasma inlet port 76, a platelet-poor plasma outlet port 78 and a platelet concentrate outlet port 80. The container 72 has a PRP outlet port 82 in communication with the inlet port 76 of the separator 74 via tubing 84. A platelet-poor plasma collection container 86 communicates with the outlet port 78 of the separator 74 via tubing 88. Finally, the platelet concentrate outlet port 80 of the separator 74 communicates with a platelet concentrate collection container 90 via tubing 92.

As an alternative, the platelet-rich plasma tubing 84 may be connected to the lower tangential port 80 of the separator 74 and the platelet concentrate tubing 92 may be connected to the upper tangential port 76 of the separator 74, the separator will operate to provide platelet concentrate using this alternative connection. However, the illustrated embodiment is preferred because it facilitates ready removal of the final aliquot of blood product from the separator 74 at the end of the procedure.

As indicated previously, the set 10 is disposable and preferably each of the first and second stage portions are separately provided in discrete flexible plastic containers or pouches indicated by the dashed lines designating portions A and B, respectively in FIG. 1. Thus, when the first stage portion is used in conjunction with the instrument illustrated in FIGS. 2 and 3, as described below, the second tubing portion may be retained in its plastic container or pouch B and disposed on an available hook on the instrument until the first stage portion is removed from the instrument and the second stage portion is applied thereto. It will be understood, however, that the first and second stage portions of the set 10 are integrally connected to each other and comprise a single closed blood collection, reinfusion and separation system. Accordingly, while the first and second stage portions A and B may be provided in discrete pouches, they are interconnected and their provision in discrete pouches is for convenience of use only as will be apparent from this description.

Figure 2:
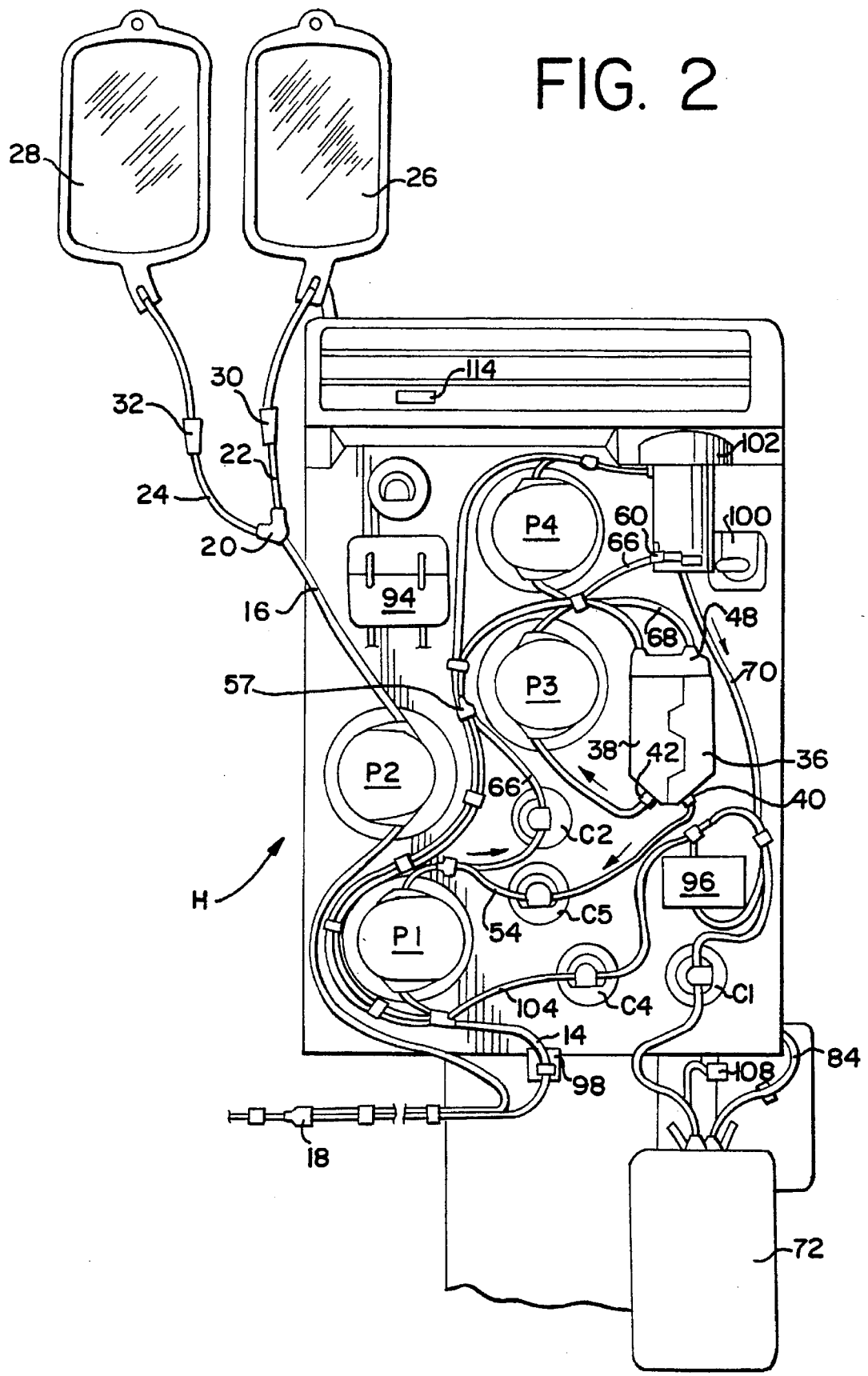
FIG. 2 is a front elevational view of an automated blood component separation instrument illustrating the first portion of the set of FIG. 1 installed in the instrument.
Figure 3:
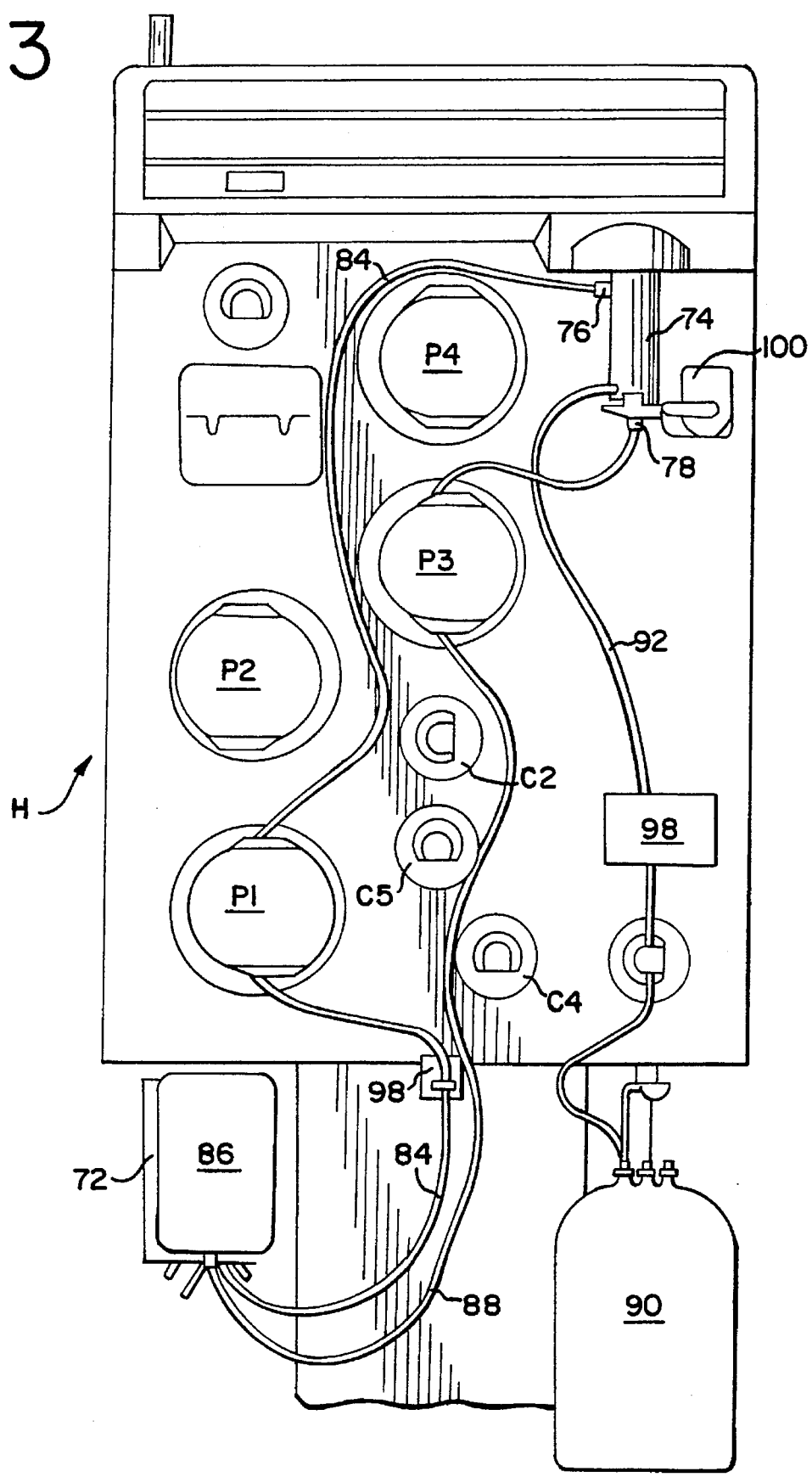
FIG. 3 is a front elevational view illustrating the automated blood component separation instrument of FIG. 2 with the second portion of the set of FIG. 1 installed in the instrument.
Figure 4:
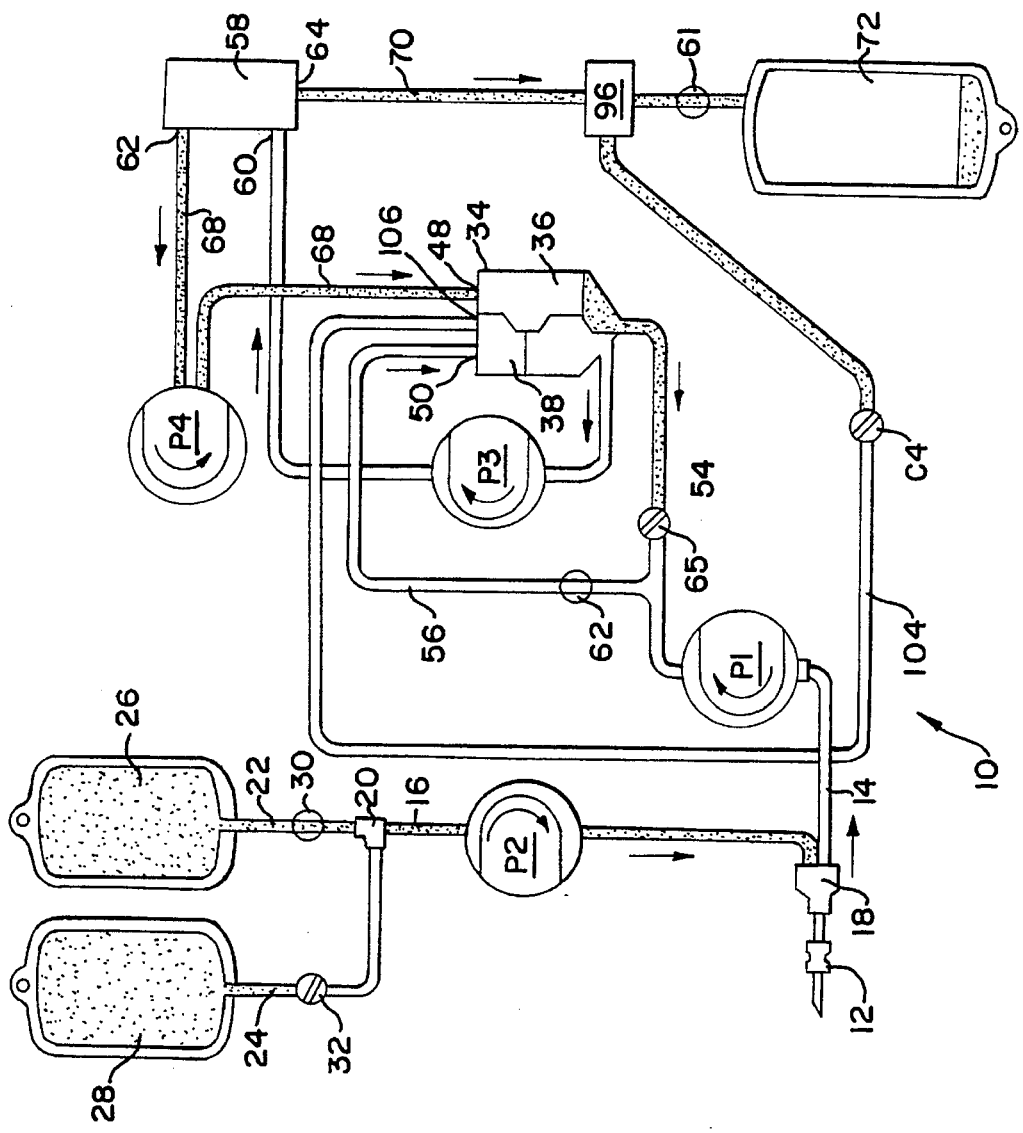
FIG. 4 is a schematic/fluid flow diagram of the blood withdrawal and separation cycle of the first stage of a platelet collection procedure using the tubing set of FIG. 1 installed in the instrument as shown in FIG. 2, wherein a first anticoagulant solution is added to the whole blood.
Figure 5:
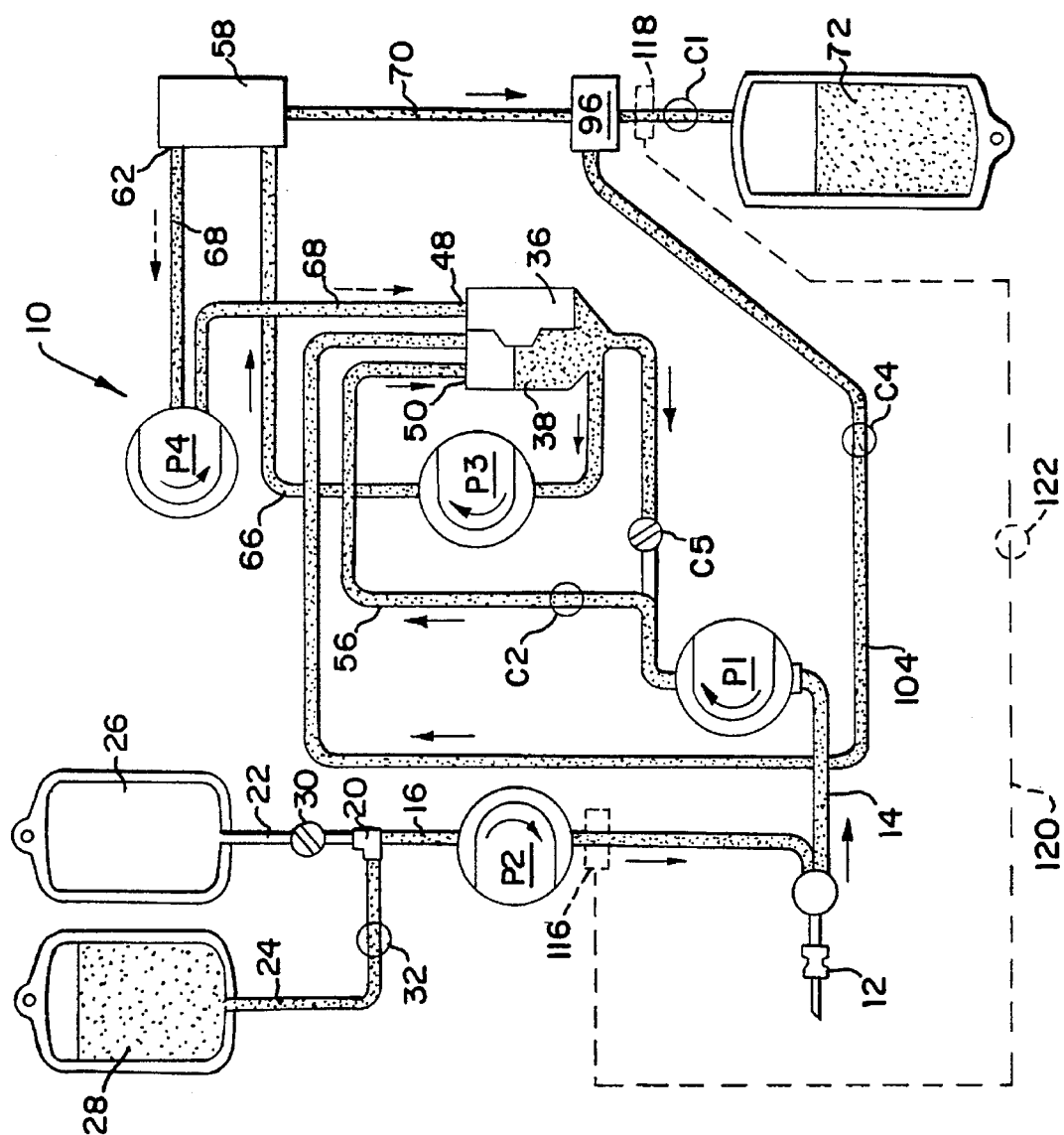
FIG. 5 is a schematic/fluid flow diagram of a different cycle of the platelet collection procedure of FIG. 4., wherein a second and different anticoagulant is added to the platelet rich plasma (PRP).

Turning now to FIGS. 2 through 5, and especially FIGS. 4 and 5, the relevant operating components of the hemapheresis instrument H will now be described. For purposes of this discussion, the hemapheresis instrument "H" described herein is the Autopheresis-C® system identified above. The instrument is provided with various pumps, detectors, clamps, and the like, under control of a microprocessor, for cooperation with the set 10 when applied to the instrument. As illustrated in FIGS. 2, 3, 4 and 5, there are provided pumps P1, P2, P3 and P4 on the front face of instrument H. These pumps are preferably of the peristaltic type and cooperate with the various tubings of set 10 thereby causing blood to flow in the desired directions between the various elements of the set. Also, a series of clamps are provided which receive the various tubing segments of the set 10. The clamps are movable between open or closed positions and thus operate to open or close the lumens of the tubing segments disposed in the clamps. For present purposes, only clamps C1, C2, C4 and C5 of instrument H need be identified.

The face of the instrument also contains a pressure transducer 94, a hemoglobin detector 96, an air detector 98, sensors (not shown) for determining the levels of liquid in reservoir 34, and a mount or lower holder 100 for the separators 58 and 74 of the set 10. The face of instrument H also includes a motor cup 102 for mounting motor magnets which, in turn, drive the separator rotors. Thus, separators 58 and 74 may be installed sequentially on lower mount 100 with their upper ends in the motor cup 102, whereby magnetic connection is effected between the magnetic drive motor and the rotor of the installed separator.

In accordance with the method of separating blood into constituent parts, the first stage portion of set 10 is installed onto the instrument face, while the second stage portion is preferably retained in its pouch B and hung from an available hook on the instrument. Under control of the microprocessor, instrument H operates pumps P1–P4, clamps C1–C5, detectors and the like in conjunction with the first stage portion of the set 10 to separate platelet-rich plasma from whole blood and reinfuse packed red cells into the donor.

During the first stage of the separation procedure, a first anticoagulant from container 26 is metered into whole blood being withdrawn from the donor. Clamp 30 on line 22 is open to allow the first anticoagulant to flow through line 22 and join blood line 14 via anticoagulant line 16. As anticoagulant from container 26 is added to the whole blood, clamp 32 remains in a closed position and prevents the flow of a second anticoagulant from container 28. After the PRP has been collected, the phlebotomy needle is removed from the donor and additional anticoagulant from container 28 is delivered to the PRP. The first stage portion is then removed from the instrument, separated from the second stage portion and discarded.

The second stage portion of the set is then installed in the instrument H as shown in FIG. 3 to generate platelet concentrate from the platelet-rich plasma. The procedure employed in the first and second stages for providing platelet concentrate will now be described in detail. These steps include the known procedure steps such as disclosed in U.S. Pat. No. 4,851,126 entitled "Apparatus and Methods for Generating Platelet Concentrate" as well as the novel method steps and apparatus for addition of two different anticoagulants.

Referring to FIGS. 2 and 4, the various tubings of the first stage portion A of set 10 are applied to instrument H as follows: blood line 14 is disposed in blood pump P1; lines 54 and 56 are disposed in clamps C5 and C2, respectively; line 66 is applied to pump P3 and line 68 is applied P4. Blood line 14 also extends through the air detector 98. The reservoir 34 is mounted on the face of the instrument, by means not shown, and the separator 58 is disposed on the mount 100 with its upper end disposed in the motor cup 102 such that the drive rotor of separator 58 is coupled magnetically to the drive motor of the instrument H. Platelet-rich plasma line 70 is disposed in hemoglobin detector 96 and clamp C1 and platelet-rich plasma container 72 is hung from a weight scale 108 on the lower part of the instrument. The second stage portion is retained in its individual pouch B which is hung from an available hook on the instrument in a non-obstructing location.

Divert line 104, which extends from the PRP line 70 to the compartment 38 at port 106 (FIG. 4), is mounted in clamp C4. Alternatively, but not important for the purpose of the present invention as seen in FIGS. 1 and 2, the divert line 104 may instead join the branch line 56 and Y-connector 57, for return to the compartment 38 at port 50.

Anticoagulant line 16 is disposed in anticoagulant pump P2 and is connected via Y connector 20 to anticoagulant containers 26 and 28. As described in detail below, two different anticoagulant formulations are used for different cycles of the separation procedure. Depending on the cycle of the separation, clamps 30 and 32 are either in the open position or closed position. When clamp 30 is open, clamp 32 is closed to allow anticoagulant from container 26 only to flow through anticoagulant line 16 to join blood line 14. Similarly, when clamp 32 is open, clamp 30 is closed allowing only anticoagulant from container 28 to flow through line 16 and join line 14 or other line.

During operation, the microprocessor of instrument H controls the instrument functions which need not be described herein. Referring now to FIG. 4, after the first stage A of set 10 is installed onto instrument H and following venipuncture performed on the donor and after priming of the separator, reservoir, the instrument in conjunction with the first stage portion A is ready to alternately collect whole blood from the donor and reinfuse packed red cells back to the donor while simultaneously and continuously supplying whole blood to the separation device to produce platelet-rich plasma and packed cells. Thus, clamp C2 is opened, clamp C5 is closed and pumps P1, P2, P3 and P4 are actuated.

In the preferred embodiment, whole blood flows through the needle 12 and blood line 14, through open clamp C2, and into whole blood compartment 38 via branch line 56 and inlet port 50 of reservoir 34. During the first stage of the operation (i.e. separation of whole blood into packed red cells and PRP) a first anticoagulant from container 26 is added to the whole blood by pump P2 via line 16 at its Y-connection with blood line 14.

As described above, clamp 30 remains in the open position so as to allow the first anticoagulant from container 26 to flow through line 22 to line 16 and ultimately join with blood line 14. In accordance with the present invention, it is preferred that the first anticoagulant solution in container 6 have a pH of at least 6.0, and more preferably between 6.5 and 7.5. One such anticoagulant is the known trisodium citrate solution (TSC) which typically has a pH in the preferred range, although TSC is believed not to have been successfully used in platelet collection procedures. Other anticoagulants meeting this criteria may also be used. Also, in accordance with the teaching of U.S. Pat. No. 5,135,667 to Schoendorfer and U.S. Pat. No. 5,171,456 to Hwang et al., it is preferred that the amount of anticoagulant added to the whole blood comprise 6% or less of the total anticoagulated whole blood volume and, most preferably 4% or less of the total anticoagulated whole blood volume. Because the preferred TSC anticoagulant typically contains a higher concentration of citrate than ACD-A (the anticoagulant described in the Schoendorfer patent), the amount of anticoagulant added to the whole blood may be further reduced to, for example, 3.3% or less of the total anticoagulated whole blood volume. In the present specification, the anticoagulant levels are calculated in the same manner as described in the patents referred to above. For example, a 6% level means 6 parts anticoagulant to 94 parts whole blood, or 6 parts anticoagulant in 100 parts anticoagulated whole blood. This is the standard system for comparing anticoagulant levels in the medical community.

Continuing with the description of the procedure, closed clamp C5 prevents flow of anticoagulated blood into reinfusion line 54. Pump P3 pumps whole blood from compartment 38 through outlet port 42 via line 66 into separator 58 via inlet port 60. Red cells are pumped from separator 58 through outlet 62 via line 68 by pump P4 into reservoir compartment 36 through inlet port 48. Platelet-rich plasma flows from separator 58 via line 60 through hemoglobin detector 96 and open clamp C1 into collection container 72. Divert clamp C4 is closed. Thus, during collection, whole blood that has been anticoagulated with a first anticoagulant solution is supplied to compartment 38 and separator 58 while packed red cells are supplied to compartment 36 and platelet-rich plasma is supplied to container 72.

The system also provides for the alternate collection of whole blood from the donor and reinfusion of packed cells into the donor while separator 58 simultaneously and continuously receives anticoagulated whole blood for separation into the platelet-rich plasma and packed cells. To accomplish this, sensors, not shown, on the instrument face detect the level of fluids in the compartments 36, 38 of the reservoir 34. When the compartments are full, the microprocessor, in response to the detected signals, causes instrument H to change from its blood collection cycle to a reinfusion cycle.

A detailed description of the reinfusion cycle is set forth in U.S. Pat. Nos. 5,135,667 to Schoendorfer and 5,171,456 to Hwang, which are incorporated by reference, and will not be repeated here. However, in general, during the reinfusion cycle clamp C2 is closed and clamp C5 is opened and the anticoagulant pump P2 is stopped. Pump P1 is reversed to pump packed cells from compartment 36 of reservoir 34 to the donor through needle 12. Pumps P3 and P4, however, continue to operate to respectively provide anticoagulated whole blood from the compartment 38 of reservoir 34 to separator 58 and to supply packed cells from separator 58 to compartment 36 of reservoir 34. When the packed cells and the supply of whole blood are substantially depleted from compartments 36 and 38, respectively, these low liquid levels are sensed. At that time, the microprocessor causes instrument H to change from its reinfusion cycle back to its blood collection cycle as shown in FIG. 4. Thus, clamp C2 is opened, clamp C5 is closed, pump P2 is started, and pump P1 is reversed to again begin the draw cycle illustrated in FIG. 4, with anticoagulated whole blood flowing to the whole blood compartment 38, which as been substantially depleted of whole blood during the reinfusion cycle. It will be appreciated that during the alternate collection and reinfusion cycles, whole blood is continuously pumped from reservoir compartment 38 to separator 58 by pump P3 whereby separation is effected continuously. Thus, platelet-rich plasma (PRP) flows continuously from separator 58, while anticoagulated whole blood is continuously supplying separator 58.

In preferred embodiments, PRP collection terminates when a preselected weight of PRP has been reached utilizing a weight scale 108. The preselected weight value may be selected by the operator for donor-specific reasons such as donor weight, donor age, etc.

When the preselected PRP weight value in the container 72 is reached, the instrument automatically transfers to a final return mode including purging the tubing of all but a small, amount of packed cells (e.g. about 10 mls). Then, the instrument automatically notifies the instrument operator to disconnect the donor. The operator uses a hemostat (not shown) or other known clamp to close the tubing segment 112 that is disposed between the phlebotomy needle 12 and the connector 18 which joins anticoagulant supply line 16 and the blood line 14. The operator may then remove the phlebotomy needle from the donor's vein. The donor may rest and then leave.

Next, the operator activates an advance button 114 (FIG. 2) on the instrument H that notifies the microprocessor control in the instrument that the donor has been disconnected. The microprocessor control then automatically advances the procedure into the new PRP-anticoagulant addition cycle illustrated in FIG. 5, so as to deliver the second anticoagulant from container 28 to the PRP in the container 72. Prior to the PRP-anticoagulant addition cycle, clamp 30 on line 22 is closed and clamp 24 on line 32 is opened to allow anticoagulant from container 28 to enter the anticoagulant line 16.

It is contemplated that the anticoagulant in container 28 (i.e. the second anticoagulant) may be different from the anticoagulant in container 26 (i.e. the first anticoagulant) added during the draw/collection cycle of the first stage. For purposes of this description, "different" means differing in any way such as pH and concentration of dextrose. For example, the second anticoagulant may have a lower pH than the first anticoagulant and contain a sufficient amount of nutrients, such as dextrose to allow for extended storage of platelets. One such anticoagulant is the known Acid-Citrate-Dextrose Solution A (ACD-A). ACD-A includes dextrose and has a pH between 4.4 and 5.5. Another anticoagulant which may be added to the PRP is Acid-Citrate-Dextrose Solution B. ACD-B includes dextrose and has a pH between 4.4 and 5.5. Still another anticoagulant that may be used is Citrate-Phosphate-Dextrose (CPD) which has a pH between 5.0 and 6.0. The amount of anticoagulant (ACD-A, for example) added to the PRP comprises between 4% and 10% and preferably between 5% and 8% of the total anticoagulated PRP volume.

It is also contemplated that the second anticoagulant can be different from the first anticoagulant in concentration of dextrose alone. For example, the second anticoagulant may have a pH similar to the pH of the first anticoagulant but, unlike the first anticoagulant, include dextrose.

In fact, it is believed preferable that the second anticoagulant have a pH higher than ACD-A, ACD-B or CPD (e.g. higher than about 6.0) and include dextrose. However, heretofore, anticoagulants with higher pH's and dextrose have been unavailable due to adverse effects on the dextrose during sterilization. Thus, it is also contemplated in the present invention that the second anticoagulant be the same as the first anticoagulant, such as dextrose-free trisodium citrate solution or any other dextrose-free anticoagulant having a higher pH, with dextrose added to the PRP separately.

The PRP-anticoagulant addition cycle is controlled by the microprocessor in the instrument. As seen in FIG. 5, pumps P1, P2 and P3 are activated. Pumps P1 and P2 pump at a speed of at least about 15 mls per minute, at most a total of about 250 mls of anticoagulant from container 28 through line 16 into blood line 14 and, as in the draw cycle illustrated in FIG. 4, clamp C2 is open and clamp C5 is closed so that pump P1 pumps anticoagulant from source 32 through branch line 56 into compartment 38 through the port 50. Input pump P3 pumps the anticoagulant from the compartment 38 into the separator 58 through tubing line 66 along with significant residual red cells in the tubing and reservoir. Pump P3 may operate at a speed of about 15 mls per minute, for example. Preferably output pump P4 is not operated. Therefore, additional packed cells accumulate within the separator 58. The rotor within the centrifugal separator 58, which normally operates in the range of approximately 2400 to 3600 rpm during the separation procedure, here operates at a speed of approximately 2000 rpm.

As the anticoagulant mixed with the residual blood cells enter by line 66 into the separator 58, where additional red cells reside, the centrifugal force within the separator separates the anticoagulant from these cells in the same manner that the separator operates to separate PRP from the donor's whole blood during the above-described separation procedure. The separated anticoagulant exits the separator 46 through port 64 and line 70, which is disposed within the hemoglobin detector 96.

At this point in the procedure, the system has been stopped for a time period in order to enable the operator to disconnect the donor from the instrument and set. Thus, the efficiency of the separator 58 will initially be less than optimal when the PRP-anticoagulant addition cycle illustrated in FIG. 5 begins. Therefore, it is likely that the first aliquot of anticoagulant flowing through line 70 during the PRP-anticoagulant addition step will have an unacceptably high concentration of red cells. If so, the hemoglobin detector 96, through the microprocessor control, will close the platelet line clamp C1 and open the divert claim C4, thereby diverting the packed cell/anticoagulant mix through divert tubing line 104 back into the reservoir compartment 38 via port 39, for subsequent recirculation into the separator 58 through the tubing line 66. As previously mentioned and as shown in FIG. 2, the divert line may alternatively join branch line 56 to reach compartment 38 via port 50.

After a short time period (approximately 30 seconds) the separator 58 will be operating with sufficient efficiency so as to meet the low hemoglobin standard set by the detector 96. Upon sensing the lower hemoglobin content, the detector 96 will instruct the microprocessor to close clamp C4 and open clamp Cl, thereby delivering the desired additional aliquot of anticoagulant to the platelet-rich plasma previously collected in the collection container 72.

By not operating the pump P4, the packed cells tend to remain in the separator, thereby lessening the volume of anticoagulant and therefore the time required to perform the PRP-anticoagulant addition setup shown in FIG. 5. The centrifugal separator itself has a low blood volume of about 30 mls. If the final tubing purge performed immediately prior to donor disconnect leaves more than the desired volume of red cells in the set 10, this may result in higher pressure within the separator 58 than is desirable for the selected efficiency range of the separator during the PRP-anticoagulant addition step. If the pressure is higher than about 320 mmHg, the pump P4 may be activated at a slow pumping rate, such as at a rate of 15 mls per minute, thereby returning some of the packed cells from the separator 58 into the reservoir compartment 36, through port 48, until the device pressure is released.

After the donor has been disconnected from the set 10, 106 and after the anticoagulant addition procedure set forth above and shown in FIG. 5, is performed, the first stage portion of the set 10 is removed from the instrument H by the operator.

The platelet-rich plasma line 70 is then heat-sealed just above the inlet port to container 72. The first stage portion may then be cut away above the seal and discarded. The second stage portion B, including container 72 with the platelet-rich plasma therein, is then applied to instrument H, illustrated in FIG. 3. It will be appreciated that in the preferred embodiment, the same particular instrument H may be used to generate PPP and platelet concentrate with set portion B as is used to generate the PRP using set portion A, although it will be recognized that this separate operation to produce the platelet concentrate may be performed on a separate instrument. Alternatively, a machine may be utilized in which set portions A and B are installed at the same time, and for example in which two needles are used (B'), for continuous draw and continuous reinfusion to the donor.

The container 72, the platelet-poor plasma container 86 and the platelet concentrate container 90 are hung from hooks conveniently disposed along the underside of the instrument. Separator 74 is disposed on mounting 100 and its upper end is disposed in mounting motor cup 102 for magnetic coupling with the drive motor of the instrument. Tubing 84 interconnecting the platelet-rich plasma container 72 and the separator 74 is disposed in pump P1 and the ultrasonic air detector 98. Tubing 88 is disposed in pump P3, while tubing 92 is disposed in the hemoglobin detector 96 and clamp C1.

To produce platelet concentrate, the microprocessor controls the instrument to actuate pump P1 to pump platelet-rich plasma from container 72 into separator 74. The rotary membrane filter of separator 74 causes the platelet-rich plasma to separate into platelet-poor plasma and platelet concentrate. The platelet-poor plasma is pumped by the pump P3 from the separator 74 via line 88 for collection in the container 86. The desired platelet concentrate flows from the separator 74 via line 92 through the hemoglobin detector 96 into platelet concentrate container 90.

The instrument is programmed such that it knows the weight of the platelet-rich plasma collected in the container 72 during the first stage. Additionally, the operator may input the instrument with the desired quantity of platelet concentrate. The pumps are controlled by the microprocessor such that the desired quantity of product is provided in the platelet concentrate collection container 90. The end of the procedure is determined when the ultrasonic air detector 98 senses air in the tube 84, thereby terminating the end of the platelet concentration cycle using the second stage of the set 10. If the final weight of the platelet concentrate suspension is low, the instrument can pump platelet-poor plasma from container 86 back through the device 74 and into the platelet concentrate container 90. If the final weight of the platelet concentrate suspension is high, the instrument can pump more platelet concentrate from container 90 back through separator 74 into the platelet-rich plasma container 72 using the procedure set forth above.

While FIG. 5 and the accompanying description set forth a preferred embodiment for adding anticoagulant to the collected PRP, by routing anticoagulant through the separation chamber 58, it will be appreciated that other means can be provided for accomplishing the addition of anticoagulant to the collected PRP. For example, a less preferred, alternate embodiment is set forth in phantom line in FIG. 5. In the alternate embodiment, a Y-connector 116 is disposed in the anticoagulant line 16 downstream of pump P2. Another Y-connector 118 is disposed in the PRP outlet line 70 downstream of the hemoglobin connector 96. A tubing segment 120 is disposed between the two Y-connectors. An associated hardware clamp 122 selectively closes and opens the tubing segment 120, for the selective addition of anticoagulant to the container 72 through the tubing segment 120. This configuration, while providing a more direct routing of anticoagulant to the container 72 results in a change to the disposable which is otherwise not needed as well as the addition of an extra clamp in the hardware. In addition, such a configuration does not take advantage of separating the small aliquot of remaining blood in the reservoir 34, unlike the preferred procedures as set forth in FIG. 5, wherein the anticoagulant in the PRP-anticoagulant addition procedure runs through the separation chamber 58.

Further alternative embodiments may also be possible with the present invention. U.S. Pat. No. 5,135,667 and U.S. Pat. No. 5,171,456 describe an additional embodiment (depicted in FIG. 7 of the above-identified patents) which is incorporated by reference herein and, for that reason, will not be discussed further.

In accordance with the present invention, by using two different anticoagulants during a platelet collection procedure, the average time required for a collection procedure can be significantly reduced without adversely affecting the platelet collection efficiency (which may actually be improved) or platelet viability during long term storage. In accordance with the present invention, it has been discovered that the reduced collection time is related to the sedimentation rate of red blood cells. In accordance with the present invention, it has further been determined that the rate of red cell sedimentation in an apheresis procedure such as the collection of platelets may be affected, at least in part, by adjusting the pH of the blood. As disclosed above, decreased collection time and increased red cell sedimentation rates may be achieved by adding an anticoagulant having a pH of at least 6.0 and, preferably a pH between 6.5 and 7.5 to the whole blood as it is being withdrawn from the donor. A series of tests were performed concerning the correlation between pH and red cell sedimentation rates. A description of these tests and results obtained are set forth below.

A. COMPARISON OF 4% ACD-A AND 10% ACD-A.

A series of tests were performed to compare the characteristics of blood anticoagulated with 4% ACD-A with blood anticoagulated with 10% ACD-A. In conducting these tests, a centrifugation fixture 126 as shown in FIG. 6 was used. The centrifugation fixture 126 comprises a stainless steel outer tube 128 closed at one end and open at the other end. The centrifugation tube was designed to receive a 6 inch length of TYGON® tubing 130 approximately ¼ to ⅜ inch I.D. A plug 132 was used to seal one end of the flexible tubing to prevent leakage of the blood within the fixture.

The stainless steel portion of the fixture has two rows of holes 134 along its length. The holes are spaced such that a sample may be obtained at 50 microliter intervals along the length of fixture. Samples may be obtained from any of the holes as desired, but the order of sample collection proceeded from the top to the bottom holes to avoid disruption of the later samples.

Volunteer donors were asked to donate blood on two separate occasions. For each donor, one of the collected blood samples was mixed with ACD-A at 4% of ACD-A per anticoagulated whole blood volume and the other sample was mixed with ACD-A at 10% of ACD-A per anticoagulated whole blood volume. Each centrifugation tube was filled with 3.5 ml ±0.1 ml of whole blood anticoagulated with either the 4% ACD-A or 10% ACD-A blood samples and placed in the centrifugation fixture. Each centrifugation fixture was then placed in a plastic bucket filled with water (for equilibration) and submitted to a centrifuge cycle in a Beckman J6-ME Centrifuge. All of the centrifugation fixtures were centrifuged for the same amount of time.

As depicted in FIG. 7, after centrifugation, a 16 gauge needle 136 attached to an automatic pipet 138 was then inserted through each hole of the outer fixture and through the inner Tygon® tubing. Fifty (50) microliter samples were taken every 100 microliters in the PRP and upper red cell layers and every 200 microliters in the lower red cell layers. Each sample was then diluted in a CellPack® saline solution. The diluted samples were measured for their concentration of red cells and platelets using a Sysmex® K1000 Cell Counter.

Figure 8:
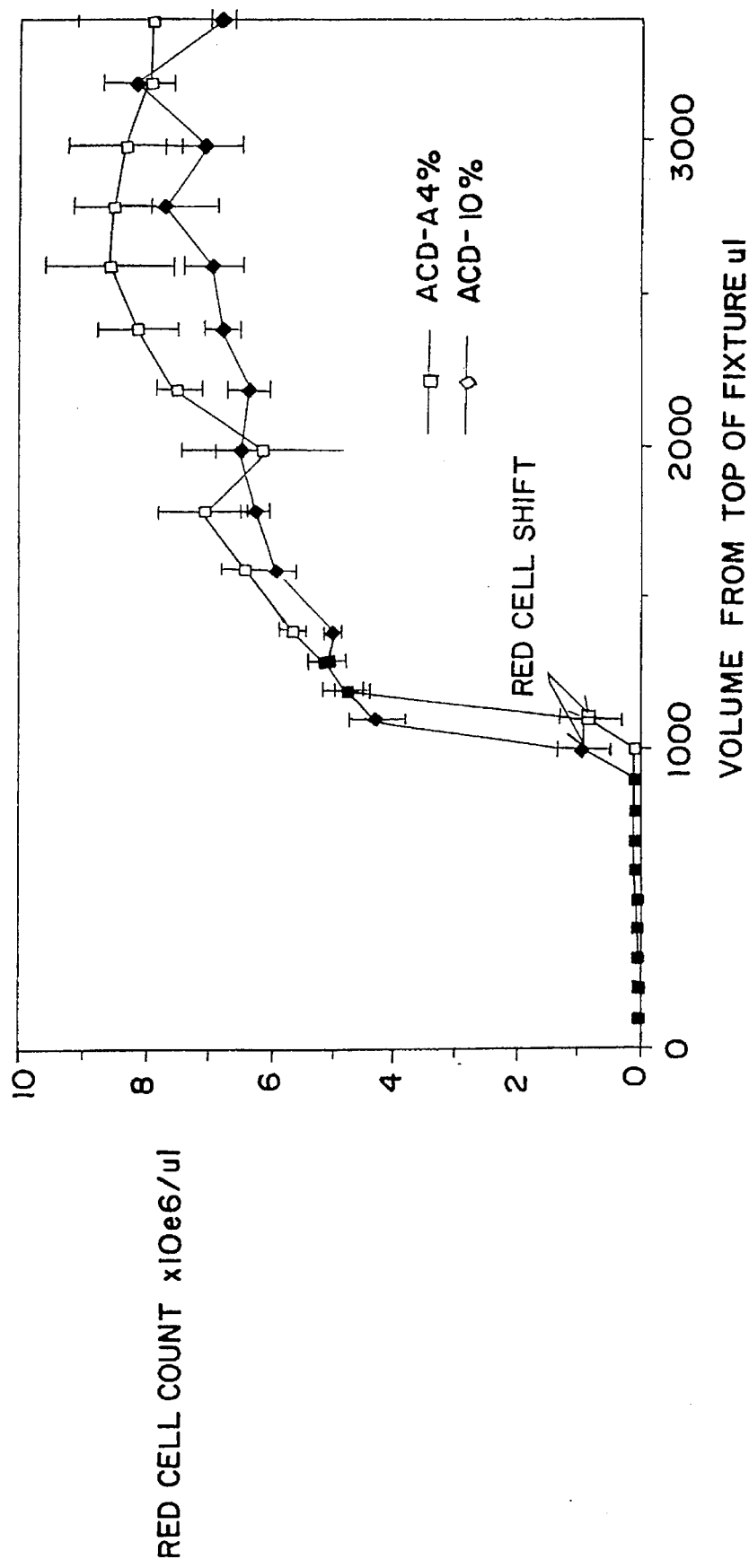
FIG. 8 is a graph that compares the position of red cells in the apparatus of FIGS. 6 and 7, when one sample of whole blood has been anticoagulated with ACD-A at 4% of anticoagulated whole blood and a sample of whole blood that has been anticoagulated with ACD-A at 10% of anticoagulated whole blood.

The results of these measurements are shown in FIG. 8. In FIG. 8, the red cell count is shown along the vertical axis and the volume from the top of the fixture (in microliters) is shown along the horizontal axis. Surprisingly, red cells were found approximately 1000 microliters from the top of the fixture in blood anticoagulated with 10% ACD-A, but at 1100 microliters in blood anticoagulated with 4% ACD-A. FIG. 8 also shows, in general, more red cells farther from the top of fixture in the 4% ACD-A samples than in the 10% ACD-A samples. Because the samples were centrifuged for the same amount of time, better and/or faster red cell sedimentation is achieved when less anticoagulant is used.

Figure 9:
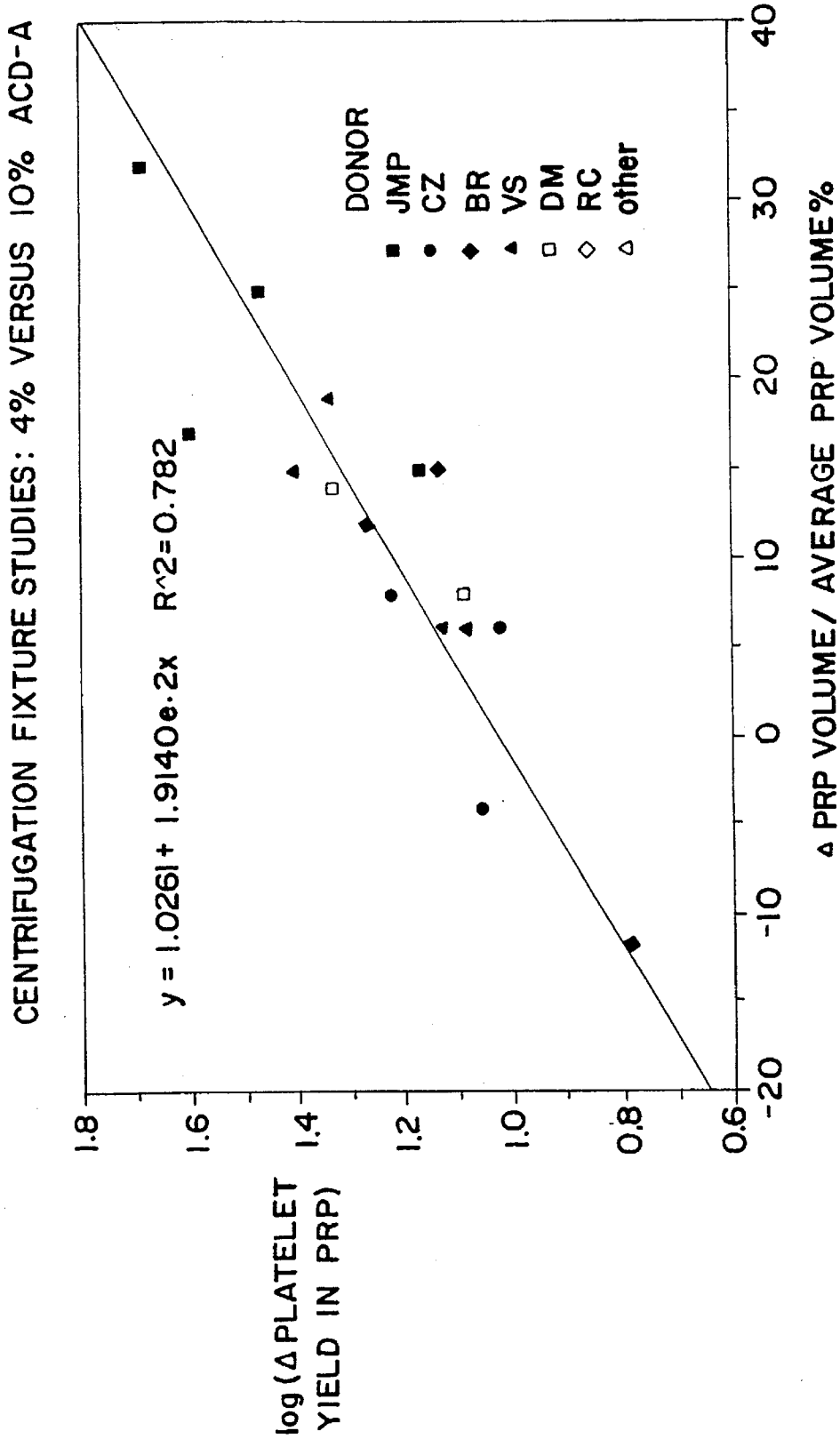
FIG. 9 is a graph that shows the increase in platelet yield relative to the change in percentage of PRP volume.

The faster the red blood cells sediment out of the PRP, the more PRP is then available for platelet collection. More PRP provides more platelets available for collection or harvesting, resulting in an increased platelet yield. For example, FIG. 9 is a graph in which the difference in PRP volume, as a percentage of average PRP volume, is set forth on the horizontal axis and the logarithm of the change in platelet yield is set forth on the vertical axis. From FIG. 9 it can be seen that the difference in platelet yield increased as the difference in the PRP volume increased. Stated a different way, this graph shows that increasing the red cell sedimentation rate to provide more PRP improves platelet yield.

Multivariable tests were also conducted concerning the effect of different variables such as anticoagulant ratio, citrate concentration, plasma tonicity, pH and dextrose concentration on the red cell sedimentation rate. Table 1 shows the compositions of the different anticoagulant formulations used for the multivariable tests.

TABLE 1

| | MULTIVARIABLE TEST - FORMULATION OF ANTICOAGULANT SOLUTIONS | | | | | |
|---|---|---|---|---|---|---|
| FORMULATION CODE | TOTAL CITRATE mM | CITRIC ACID mM | TRISODIUM CITRATE mM | DEXTROSE mM | PH | TONICITY* mOsm |
| C | 120 | 0.6 | 119.4 | 124 | 7.4 | 600 |
| B | 120 | 0.6 | 119.4 | 0 | 7.4 | 600 |
| I | 120 | 40.0 | 80.0 | 124 | 5.0 | 300 |
| A | 120 | 40.0 | 80.0 | 0 | 5.0 | 300 |
| E | 120 | 40.0 | 80.0 | 124 | 4.9 | 600 |
| G | 120 | 40.0 | 80.0 | 0 | 4.9 | 600 |
| J | 60 | 0.4 | 59.6 | 0 | 7.4 | 300 |
| D | 60 | 0.3 | 59.7 | 124 | 7.4 | 600 |
| K | 60 | 40.0 | 20.0 | 124 | 3.7 | 300 |

*adjusted with sodium chloride

Blood was collected from 10 donors (6 high hematocrit donors and 4 low hematocrit donors, 5 men and 5 women) and was distributed among the anticoagulant solutions C,B, I,A,E,G,J,D and K as set forth in Table 1. Blood collected in three anticoagulant solutions L,F and H (not listed) clotted during initial experiments. Accordingly, these anticoagulant solutions were not tested further.

Table 2 shows the different anticoagulant formulations C,B,I,A,E,G,J,D and K (Column 1), the trial numbers assigned to each individual test sample (Column 2), the characteristics of each formulation (Columns 3 through 6), the anticoagulant ratios used (Column 7) and the hematocrit levels of the donors (Column 8).

More specifically, as shown in the third column of Table 2, the different anticoagulant formulations included high citrate concentrations of 120 mM or low citrate concentrations of 60 mM. As shown in Column 4 of Table 2, the blood collected from the donors was mixed with an anticoagulant having a pH of 7.4 to achieve a "high" blood pH or an anticoagulant having a pH between 3.7 and 5.0 to achieve a "low" blood pH. Column 5 of Table 2 shows that the solutions were either "iso" meaning isotonic (300 mOsm) or "hyper", meaning hypertonic (600 mOsm.) Column 6 shows that some of the anticoagulant formulations either contained dextrose (124 mM) or were free of dextrose. The anticoagulant ratios used for the multivariable test included "high" ratios of 10% or "low" ratios of 4% as shown in column 7 of Table 2. High hematocrit donors had hematocrits of 40 or greater and low hematocrit donors had hematocrits of less than 40 (column 8, Table 2).

For purposes of these tests, simple graduated plastic sedimentation tubes commonly referred to as Westergren Pipettes available from Scientific Products, Inc. as Disposable Pipette No. B4515-10 were used. Each sedimentation tube was filled with approximately 1.25 ml of a different anticoagulated whole blood sample. Each sedimentation tube was mounted vertically in a horizontal stand and placed in a room maintained at 20°–21° C.

The position of the plasma/red cell interface was ascertained visually and recorded at different time intervals. A sedimentation velocity was then calculated as the variation in the interface level (in millimeters) divided by the elapsed time in minutes. A sedimentation velocity was calculated for each anticoagulant formulation at the time the first anticoagulated blood specimen reached its maximum velocity. This measurement was referred to as the "maximum relative sedimentation velocity" (MRSV).

Using the ECHIP™ statistical analysis computer software program, the effect of certain variables such as donor hematocrit, anticoagulant ratio, citrate concentration, glucose concentration, plasma tonicity and pH on the sedimentation velocity was analyzed.

Figure 10:
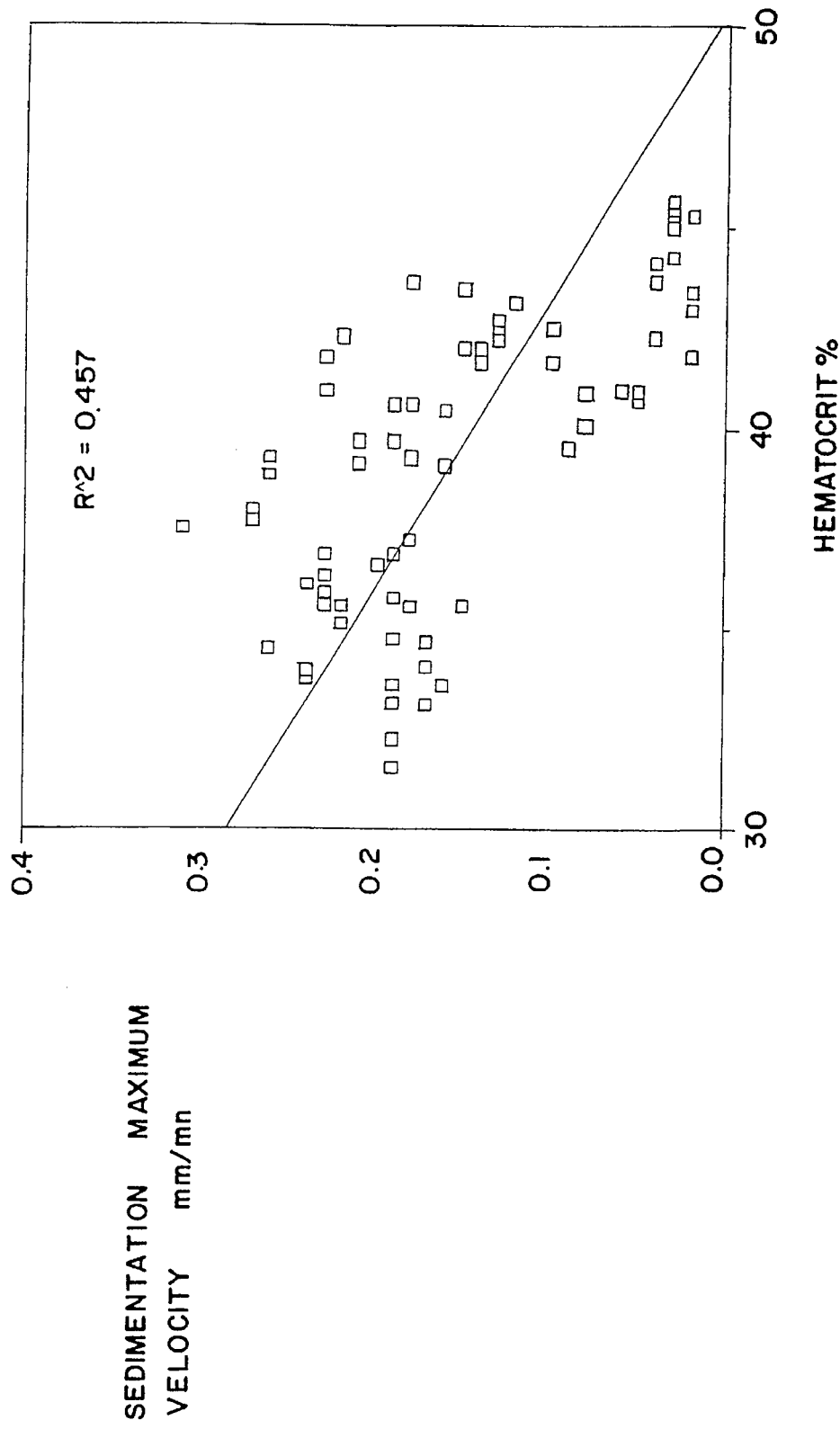
FIG. 10 is a graph that shows the sedimentation velocity of red cells in whole blood having different hematocrits.

One factor which had an effect on the sedimentation velocity MRSV was the donor hematocrit. This "donor effect" is shown in FIG. 10. The maximum sedimentation velocity of red cells is set forth on the vertical axis of FIG. 10 and the donor hematocrit is set forth on the horizontal axis. As can be seen from FIG. 10, the lower the hematocrit of the donor, the higher the sedimentation velocity of red cells.

TABLE 2

ANTICOAGULANT FORMULAS AND DONOR HEMATOCRIT LEVELS

| FORMULA | TRIAL | CITRATE | BLOOD PH | TONICITY | DEXTROSE | AC RATIO | HEMATOCRIT |
|---|---|---|---|---|---|---|---|
| C | 3 | HIGH | HIGH | HYPER | YES | HIGH | HIGH |
| C | 3 | HIGH | HIGH | HYPER | YES | HIGH | HIGH |
| C | 19 | HIGH | HIGH | HYPER | YES | HIGH | LOW |
| C | 20 | HIGH | HIGH | HYPER | YES | LOW | LOW |
| C | 23 | HIGH | HIGH | HYPER | YES | LOW | HIGH |
| B | 2 | HIGH | HIGH | HYPER | NO | LOW | LOW |
| B | 2 | HIGH | HIGH | HYPER | NO | LOW | LOW |
| B | 6 | HIGH | HIGH | HYPER | NO | LOW | HIGH |
| B | 6 | HIGH | HIGH | HYPER | NO | LOW | HIGH |
| I | 9 | HIGH | LOW | ISO | YES | HIGH | LOW |
| I | 13 | HIGH | LOW | ISO | YES | HIGH | HIGH |
| A | 1 | HIGH | LOW | ISO | NO | LOW | HIGH |
| A | 1 | HIGH | LOW | ISO | NO | LOW | HIGH |
| A | 16 | HIGH | LOW | ISO | NO | LOW | LOW |
| A | 16 | HIGH | LOW | ISO | NO | LOW | LOW |
| E | 5 | HIGH | LOW | HYPER | YES | LOW | HIGH |
| E | 5 | HIGH | LOW | HYPER | YES | LOW | HIGH |
| E | 17 | HIGH | LOW | HYPER | YES | LOW | LOW |
| E | 17 | HIGH | LOW | HYPER | YES | LOW | LOW |
| E | 18 | HIGH | LOW | HYPER | YES | HIGH | LOW |
| E | 22 | HIGH | LOW | HYPER | YES | HIGH | HIGH |
| G | 7 | HIGH | LOW | HYPER | NO | HIGH | LOW |
| G | 12 | HIGH | LOW | HYPER | NO | HIGH | HIGH |
| G | 15 | HIGH | LOW | HYPER | NO | LOW | HIGH |
| G | 24 | HIGH | LOW | HYPER | NO | LOW | LOW |
| J | 10 | LOW | HIGH | ISO | NO | HIGH | LOW |
| J | 14 | LOW | HIGH | ISO | NO | HIGH | HIGH |
| D | 4 | LOW | HIGH | HYPER | YES | HIGH | LOW |
| D | 4 | LOW | HIGH | HYPER | YES | HIGH | LOW |
| D | 8 | LOW | HIGH | HYPER | YES | HIGH | HIGH |
| D | 8 | LOW | HIGH | HYPER | YES | HIGH | HIGH |
| K | 11 | LOW | LOW | ISO | YES | HIGH | HIGH |
| K | 21 | LOW | LOW | ISO | YES | HIGH | LOW |

In order to measure the effect of the anticoagulant formulation (i.e the "solution effect") on the sedimentation velocity and eliminate "inter donor" variation, a relative difference in MRSV was calculated for each donor. The relative difference of MRSV expressed in % was calculated for an anticoagulant X and a donor Y according to the following formula;

Relative $\Delta MRSV\%_{xy} = (MRSV_{xy} - MRSV_{ly})/MRSV_{xy} \times 100$

Where $MRSV_{xy}$ is the measured MRSV for the anticoagulant X and donor y; and $MRSV_{ly}$ is the lowest measured MRSV for a given donor Y based on the tested anticoagulants.

Based on the foregoing, the relative difference in MRSV was determined to be primarily related to the blood pH. Specifically, the higher the pH, the higher the relative difference in MRSV. Stated another way, using an anticoagulant having a high pH caused the relative sedimentation velocity of red cells in a given donor's blood to increase.

There was also a correlation between the relative difference in MRSV and the red cell size expressed as MCV (mean corpuscular volume). The higher the MRSV, the lower the MCV, suggesting that the higher the blood pH, the smaller the MCV of the red cells. Concentrations of glucose, citrate and plasma tonicity were found to have little effect on MRSV and are not reported herein.

Further tests were conducted to compare the sedimentation rates in whole blood anticoagulated with 4% ACD-A solution and 3.3% trisodium citrate solution (TSC). 3.3% TSC was chosen to provide a concentration of citrate equivalent to the concentration of citrate in the 4% ACD-A and thereby eliminate any possible effect of citrate. The pH of TSC was measured at 6.6 and the pH of ACD-A was measured at 4.9. Using sedimentation tubes and a procedure as described above in connection with the multivariable tests the MRSV of blood anticoagulated with 3.3% TSC was found to be significantly higher than the MRSV of blood anticoagulated with 4% ACD-A in all but one donor. The results of these tests are set forth in Table 3. As shown in Table 3, the difference in MRSV was 18% faster in the samples with 3.3% TSC.

The effect of pH on the red cell sedimentation rate is further confirmed in Table 4. In line 2 of Table 4 two different anticoagulants, 3.3% TSC and 4.0% ACD-A, having equal concentrations of citrate but varying in pH and the concentration of dextrose are compared. In particular, the pH of 4% ACD-A was 4.9 and the pH of 3.3% TSC was 6.6. ACD-A contained dextrose and TSC was free of dextrose. As seen in Table 4, using 3.3% TSC resulted in greater MRSV of red cells by an average of 18% over the MRSV of red cells in 4% ACD-A. Although the difference in the dilution factor may have some effect on the increase in MRSV, the difference in dilution between 3.3% TSC and 4% ACD-A is believed to be substantially negligible.

In line 3 of Table 4, two different anticoagulants, TSC and ACD-A having the same pH 7.4 are compared. This comparison was meant to show the effect, if any, of dextrose on the MRSV. It will be recalled that ACD-A includes dextrose, while TSC is free of dextrose. As shown in line 3 of Table 4, dextrose had almost no effect on the MRSV, when the pH of both anticoagulants was the same.

Figure 11:
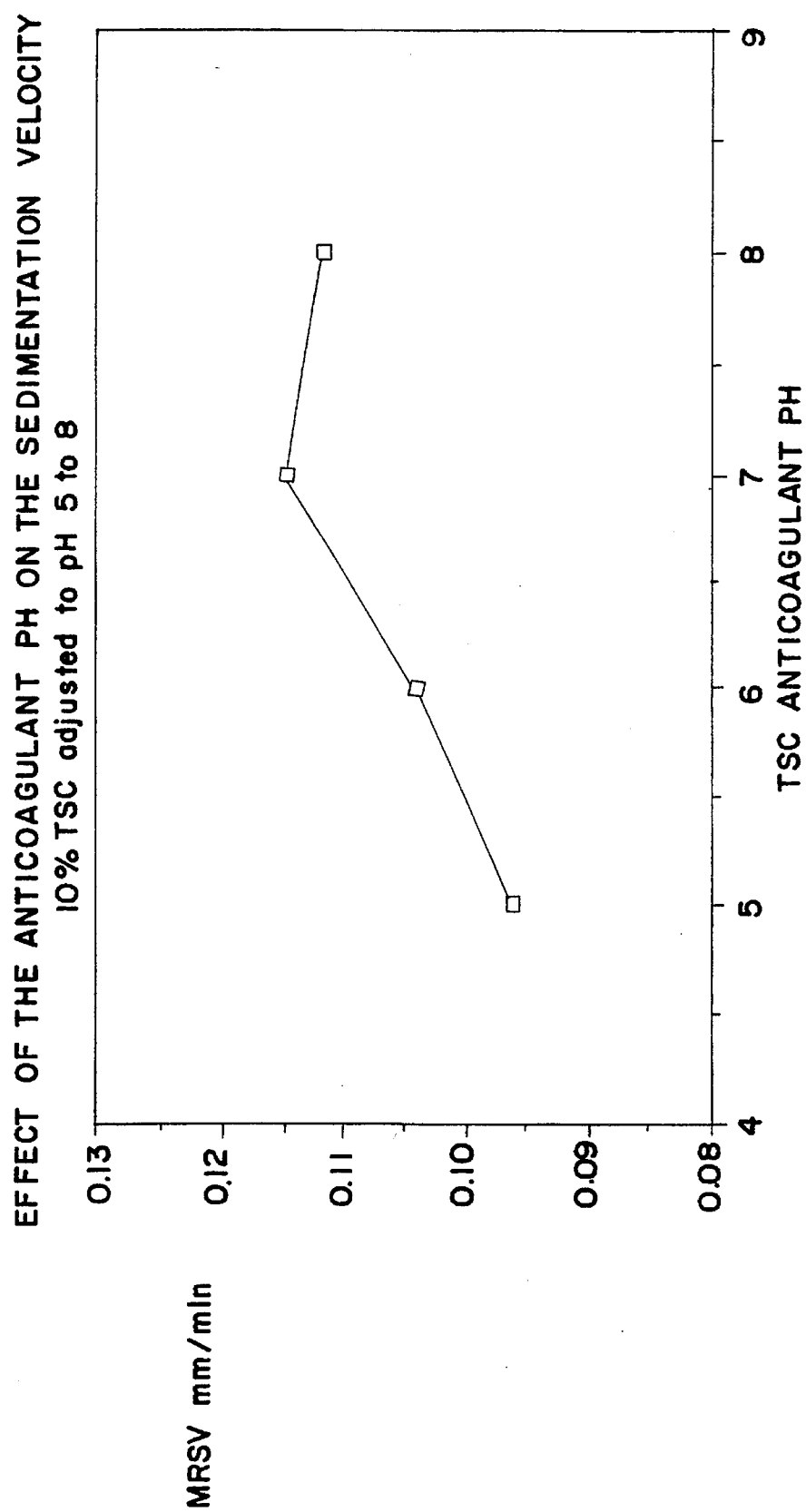
FIG. 11 is a graph which shows the relative difference in the sedimentation velocity of red cells in samples of whole blood that have been mixed with anticoagulants of different pH.

Finally, the effect of pH on MRSV is further depicted in FIG. 11.

TABLE 3

MAXIMUM RELATIVE SEDIMENTATION VELOCITY (MISV)
3.3% TSC V. 4% ACD-A

| DONOR | MRSV mm/mn - 3.3% TSC | | MRSV mm/mn - 4% ACD-A | | ΔMRSV mm/mn | ΔMRSV % |
|---|---|---|---|---|---|---|
| | AVERAGE* | STD. DEV* | AVERAGE* | STD. DEV.* | | |
| MMC | 0.30 | 0.02 | 0.27 | 0.01 | 0.03 | 11 |
| LH | 0.21 | 0.00 | 0.20 | 0.01 | 0.01 | 5 |
| DM | 0.40 | 0.04 | 0.39 | 0.05 | 0.01 | 3 |
| LP | 0.37 | 0.03 | 0.32 | 0.01 | 0.05 | 16 |
| BRH | 0.20 | 0.00 | 0.21 | 0.00 | −0.01 | −5 |
| LB | 0.22 | 0.00 | 0.19 | 0.00 | 0.03 | 16 |
| OM | 0.02 | 0.00 | 0.01 | 0.00 | 0.01 | 100 |
| AK | 0.41 | 0.02 | 0.37 | 0.01 | 0.04 | 11 |
| CB | 0.24 | 0.01 | 0.22 | 0.01 | 0.02 | 9 |
| JH | 0.17 | 0.01 | 0.13 | 0.01 | 0.04 | 31 |
| DF | 0.31 | 0.01 | 0.28 | 0.01 | 0.03 | 11 |
| DB | 0.26 | 0.01 | 0.23 | 0.00 | 0.03 | 13 |
| AVERAGE | | | | | 0.02 | 18 |
| STD DEV | | | | | 0.02 | 27 |

*average and standard deviation of 2 sedimentation tubes

TABLE 4

PAIRED COMPARISON OF RED CELL MRSV ACCORDING TO THE ANTICOAGULANT REGIMEN. DATA IS AVERAGE OF 12 EXPERIMENTS FOR EACH ANTICOAGULANT PAIR

| ANTICOAGULANT A | MRSV (mm/min) | ANTICOAGULANT B | MRSV (mm/min) | ΔMRSV (mm/min) | ΔMRSV (%) |
| --- | --- | --- | --- | --- | --- |
| 4% ACD-A | 0.27 +/− 0.16 | 10% ACD-A | 0.20 +/− 0.13 | 0.07 +/− 0.04 | 40 +/− 0.04 |
| 3.3% TSC | 0.26 +/− 0.11 | 4% ACD-A | 0.24 +/− 0.10 | 0.02 +/− 0.02 | 18 +/− 27 |
| 4% ACD-A pH 7.4 | 0.19 +/− 0.11 | 4% TSC pH 7.4 | 0.19 +/− 0.11 | 0.00 +/− 0.01 | 2 +/− 5 |
| 4% TSC pH 7.4 | 0.21 +/− 0.12 | 10% TSC pH 7.4 | 0.17 +/− 0.11 | 0.04 +/− 0.03 | 28 +/− 27 |

In particular, the sedimentation velocity (expressed as MRSV) is set forth on the vertical axis and the pH of 10% TSC anticoagulant added to whole blood is set forth on the horizontal axis. As can be seen from FIG. 11, blood mixed with an anticoagulant having a low pH of 5 exhibited a lower sedimentation rate than blood mixed with an anticoagulant having a high pH of 7.

As presently understood, the effect of pH and anticoagulant ratio on red cell sedimentation is as follows. Typically, the anticoagulants that have been used for platelet collections (ACD-A and ACD-B, for example) have a pH of between 4.4 and 5.5. Accordingly, adding more ACD-A (10%, for example) to whole blood lowers the overall pH of blood, whereas adding a smaller amount of ACD-A (4%) maintains the pH of blood closer to its normal value of approximately 7.4. Thus, improved red cell sedimentation may be obtained by adding to the whole blood an anticoagulant having a higher starting pH. For example, adding an anticoagulant, such as TSC, which has a pH closer to the pH of whole blood will not lower the overall pH of the blood as much as the same amount of an anticoagulant having a low pH. Alternatively, ACD-A may be used and the pH of whole blood may be separately adjusted to a near normal level.

Based on this observed effect of pH on the red cell sedimentation rate, platelet collection procedures were performed on the Autopheresis C® system. For purposes of these tests, 4% TSC having a pH of approximately 6.7 was added to whole blood during the draw/collection cycle of the first stage (i.e. wherein whole blood is withdrawn from a donor and is separated into red cells and PRP) with 7% ACD-A having a pH of 4.9 per total anticoagulated platelet-rich plasma being added to the PRP prior to the platelet concentrate phase. The platelet collection procedures using the above described anticoagulant regimen are hereinafter referred to as the "TSC runs". Approximately 14 donors were used for this study and three separate procedures at three different separator speeds (3600 rpm, 3000 rpm and 2700 rpm) were performed. Collection times, PRP volume, PRP yield, PRP efficiency and white blood cell count in PRP were all measured.

The results of these TSC runs were then compared to earlier platelet collection procedures performed on the same donors using only ACD-A. These procedures are hereinafter referred to as the ACD-A runs. In these ACD runs, whole blood was anticoagulated with 4% ACD-A per anticoagulated whole blood volume during the draw/collection cycle of the first stage with additional 7% ACD-A per total anticoagulated PRP volume being added to the PRP before the platelet concentration phase. For these ACD-A runs, the separator speed was adjusted to the recommended setting of 3600 rpm. The following Tables 5, 6, 7 summarize the results of the TSC runs and the ACD-A runs.

As seen in Table 5, whole blood with 4% TSC centrifuged at 3600 rpm showed a significant improvement in collection time as compared to whole blood mixed with 4% ACD-A. The average collection time for a platelet collection procedure using 4% TSC was 60 minutes whereas the average collection time using ACD-A was 71 minutes. Average PRP volume was greater for the TSC runs than for ACD-A, and platelet yields were sufficiently close to be considered approximately the same for both anticoagulant formulations. Similarly, PRP efficiency for the two anticoagulant formulations was approximately the same. (To calculate PRP efficiency, the volume of the PRP collected is multiplied by the concentration of platelets in the PRP, the product forming the numerator. The denominator is the product of the platelet concentration in the donor's anticoagulated whole blood at the beginning of the procedure (i.e. donor precount) multiplied by the volume of whole blood processed.

Table 6 compares the TSC runs performed at 3000 rpm and the ACD-A runs performed at 3600 rpm. Although the difference in collection time was not as significant as in Table 5, the average collection time was still approximately 5 minutes less for the TSC runs than for the ACD-A runs. PRP volume was greater for the TSC runs and both platelet yield and platelet efficiency were improved using TSC.

Table 7 shows TSC runs performed at 2700 rpm and the ACDA runs performed at 3600 rpm. These runs did not, however, result in further improvement in run times, PRP volumes, yields or efficiencies.

These tests indicate that under certain run conditions and using certain anticoagulants having a pH higher than the pH in anticoagulants typically used for platelet procedures, shorter collection times may be achieved without a significant difference in the improved platelet yields and efficiencies first reported by Schoendorfer. Platelets collected using 4% TSC per anticoagulated whole blood volume as the first anticoagulant and 7% ACD-A per total anticoagulated PRP volume (i.e. 7% ACD-A and 93% PRP) as the second anticoagulant also maintained their viability during long term (5-day) storage.

TABLE 5

TSC RUNS AT 3600 RPM$_{max}$ V. ACD-A RUNS AT 3600 RPM$_{max}$

| DONOR | TOTAL TIME (MINUTES) | | HCT PRE (%) | | PRP VOL (ml) | | PRP YIELD ($\times 10^{11}$ plts/unit) | | PRP EFF (%) | |
|---|---|---|---|---|---|---|---|---|---|---|
| | TSC | ACD-A | TSC | ACD-A | TSC | ACD-A | TSC | ACD-A | TSC | ACD-A |
| CSM | 48 | 62 | | 39 | 636 | 625 | 3.4 | 4.8 | 48% | 46% |
| LHE | 60 | 75 | 38 | 41 | 733 | 603 | 1.6 | 2.3 | 31% | 39% |
| BRI | 76 | 86 | | 45 | 743 | 598 | 4.2 | 3.9 | 41% | 31% |
| RMH | 57 | 67 | 38 | 39 | 738 | 702 | 2.8 | 2.8 | 55% | 48% |
| MDO | 43 | 62 | 36 | 37 | 641 | 585 | 2.7 | 2.8 | 47% | 43% |
| DMA | 55 | 68 | 38 | 39 | 732 | 681 | 1.8 | 2.5 | 36% | 41% |
| NGR | 46 | 58 | 36 | 38 | 634 | 642 | 3.3 | 4.5 | 52% | 54% |
| BRH | 97 | 91 | 45 | 45 | 638 | 575 | 4.0 | 3.1 | 38% | 38% |
| AVERAGE | 60 | 71 | 39 | 40 | 687 | 626 | 3.0 | 3.4 | 44% | 43% |
| STD DEV | 18 | 12 | 4 | 3 | 53 | 46 | 0.9 | 0.9 | 8% | 7% |

TABLE 6

TSC RUNS AT 3000 RPM$_{max}$ V. ACD-A RUNS AT 3600 RPM$_{max}$

| DONOR | TOTAL TIME (MINUTES) | | HCT PRE (%) | | PRP VOL (ml) | | PRP YIELD ($\times 10^{11}$ plts/unit) | | PRP EFF (%) | |
|---|---|---|---|---|---|---|---|---|---|---|
| | TSC | ACD-A | TSC | ACD-A | TSC | ACD-A | TSC | ACD-A | TSC | ACD-A |
| LBR | 49 | 58 | 34 | 37 | 636 | 611 | 2.7 | 2.3 | 39% | 40% |
| CBE | 58 | 63 | 35 | 37 | 638 | 622 | 2.8 | 3.1 | 51% | 49% |
| DFA | 67 | 54 | 36 | 36 | 633 | 620 | 3.9 | 3.8 | 37% | 43% |
| DBR | 45 | 58 | 33 | 35 | 633 | 613 | 3.5 | 2.5 | 51% | 47% |
| DAK | 57 | 76 | 39 | 41 | 628 | 646 | 5.4 | 4.5 | 50% | 40% |
| LIK | 52 | 63 | 35 | 36 | 629 | 598 | 2.1 | 2.1 | 42% | 39% |
| MAB | 64 | 61 | 36 | 38 | 634 | 543 | 1.6 | 1.6 | 30% | 32% |
| DIR | 56 | 56 | 37 | 39 | 728 | 603 | 4.7 | 4.0 | 47% | 38% |
| STT | 86 | 75 | 44 | 40 | 733 | 682 | 4.2 | 3.8 | 45% | 46% |
| SEV | 70 | 74 | 40 | 40 | 740 | 647 | 5.6 | 5.7 | 51% | 44% |
| BOV | 63 | 67 | 40 | 39 | 636 | 617 | 4.0 | 4.5 | 43% | 44% |
| ELH | 40 | 52 | 36 | 36 | 628 | 610 | 2.8 | 3.0 | 63% | 49% |
| VIO | 45 | 59 | 39 | 39 | 642 | 603 | 3.3 | 3.9 | 52% | 44% |
| AVERAGE | 58 | 63 | 37 | 38 | 657 | 617 | 3.6 | 3.4 | 46% | 43% |
| STD DEV | 12 | 8 | 3 | 2 | 44 | 32 | 1.2 | 1.1 | 8% | 5% |

TABLE 7

TSC RUNS AT 2700 RPM$_{max}$ V. ACD-A RUNS AT 3600 RPM$_{max}$

| DONOR | TOTAL TIME (MINUTES) | | HCT PRE (%) | | PRP VOL (ml) | | PRP YIELD ($\times 10^{11}$ plts/unit) | | PRP EFF (%) | |
|---|---|---|---|---|---|---|---|---|---|---|
| | TSC | ACD-A | TSC | ACD-A | TSC | ACD-A | TSC | ACD-A | TSC | ACD-A |
| DOK | 81 | 70 | 37 | 39 | 607 | 612 | 2.2 | 2.2 | 38% | 38% |
| CSM | 66 | 62 | 38 | 39 | 634 | 625 | 3.9 | 4.8 | 41% | 46% |
| TOD | 93 | 81 | 39 | 41 | 735 | 658 | 2.3 | 2.9 | 27% | 48% |
| BRH | 101 | 91 | 42 | 45 | 593 | 575 | 2.3 | 3.1 | 23% | 38% |
| CAA | 101 | 92 | 42 | 44 | 583 | 573 | 1.8 | 2.6 | 25% | 31% |
| DIR | 55 | 59 | 35 | 38 | 636 | 581 | 3.1 | 2.9 | 41% | 43% |
| JOH | 100 | 92 | 44 | 48 | 735 | 654 | 3.4 | 3.8 | 33% | 41% |
| NIG | 47 | 58 | 38 | 38 | 344 | 642 | 2.1 | 4.5 | 26% | 54% |
| MAS | 54 | 69 | 37 | 40 | 632 | 610 | 4.0 | 4.3 | 45% | 38% |
| AVERAGE | 78 | 75 | 39 | 41 | 611 | 614 | 2.8 | 3.4 | 33% | 42% |
| STD DEV | 22 | 14 | 3 | 4 | 114 | 33 | 0.8 | 0.9 | 8% | 7% |

The present invention has been described in terms of the preferred embodiment. However, as will be appreciated by those of ordinary skill, other embodiments of the present invention are also possible. For example, the above disclosure has been intended to describe the present invention as used in conjunction with the Autopheresis C® system. It will be understood, however, that the present invention is not limited to the Autopheresis C®, but may also be utilized in conjunction with other apheresis instruments such as the CS3000 ®, which is a centrifugal cell separator The above disclosure is also intended to include various further modifications included within the spirit and scope of the appended claims.

That which is claimed:

1. A method for separating platelets and red cells in whole blood comprising:
   a) providing a quantity of whole blood comprising at least red blood cells, platelets and plasma;
   b) adding a first anticoagulant to the whole blood to provide a mixture of whole blood and anticoagulant, said first anticoagulant having a pH that is at least about 6.0 and is effective to increase the rate of red cell sedimentation;
   c) separating the red cells from the platelets by allowing the red blood cells in said mixture to sediment; and
   d) adding a second and different anticoagulant to the separated platelets.

2. The method of claim 1 wherein the first anticoagulant has a pH between 6.5 and 7.5.

3. The method of claim 1 wherein the amount of said first anticoagulant comprises 4% or less of the total anticoagulated whole blood volume.

4. The method of claim 1 wherein the amount of said first anticoagulant comprises 3.3% of the total anticoagulated whole blood volume.

5. The method of claim 1 wherein the amount of the first anticoagulant comprises 4% or less of the total anticoagulated whole blood volume and the pH of said first anticoagulant is at least 6.0.

6. The method of claim 1 wherein the second anticoagulant is an anticoagulant other than trisodium citrate solution.

7. The method of claim 1 wherein the second anticoagulant is selected from the group consisting of ACD-A, ACD-B, and CPD.

8. The method of claim 1 wherein the second anticoagulant is ACD-A.

9. The method of claim 1 wherein said second anticoagulant includes dextrose.

10. The method of claim 1 wherein the amount of the said second anticoagulant comprises between 4% and 10% of the total anticoagulated platelet volume.

11. The method of claim 1 wherein said first anticoagulant is trisodium citrate solution and the second anticoagulant is an anticoagulant other than trisodium citrate solution.

12. The method of claim 1 wherein the first anticoagulant is trisodium citrate solution and the second anticoagulant is selected from the group consisting of ACD-A, ACD-B, and CPD.

13. The method of claim 1 wherein the first anticoagulant is trisodium citrate solution and the second anticoagulant is ACD-A.

14. The method of claim 1 wherein said first anticoagulant is free of dextrose and said second anticoagulant includes dextrose.

15. The method of claim 1 wherein said second anticoagulant is free of dextrose, said method further comprising the step of separately adding dextrose to said platelets.

16. The method of claim 1 wherein said first anticoagulant is selected to increase the rate of red cell sedimentation and said second anticoagulant is selected to provide for long-term storage of platelets.

17. The method of claim 1 wherein the first anticoagulant has a pH between 6.5 and 7.5 and the amount of said first anticoagulant is equal to or less than 4% of the total anticoagulated whole blood volume and said second anticoagulant comprises between 4% and 10% of the total anticoagulated platelet volume.

18. The method of claim 1 wherein said second and different anticoagulant is added to platelets in plasma.

19. The method of claim 1 further comprising concentrating the platelets to form a platelet concentrate and adding said second and different anticoagulant to said platelet concentrate.

20. A system for separating platelets from whole blood, said system comprising:
   a) a separation chamber for separating platelets from whole blood;
   b) an upstream flow path including a whole blood source, said upstream flow path communicating with said separation chamber for providing whole blood to said separation chamber;
   c) a downstream flow path communicating with said separation chamber for transporting platelets from said separation chamber;
   d) a first anticoagulant source for introducing a first anticoagulant into said upstream flow path, said first anticoagulant having a pH that is at least about 6.0 and is effective to increase the rate of red cell sedimentation;
   e) a second anticoagulant source for introducing a second and different anticoagulant into said downstream flow path or said separation chamber; and
   f) an anticoagulant flow path for connecting said first anticoagulant source with said upstream flow path and for connecting said second anticoagulant source with said downstream flow path.

21. The system of claim 20 wherein said first anticoagulant has a pH between 6.5 and 7.5.

22. The system of claim 20 wherein said first anticoagulant is trisodium citrate solution.

23. The system of claim 20 wherein the second anticoagulant is an anticoagulant other than trisodium citrate solution.

24. The system of claim 20 wherein the second anticoagulant is selected from the group consisting of ACD-A, ACD-B, and CPD.

25. The system of claim 20 wherein said second anticoagulant is ACD-A.

26. The system of claim 20 wherein said first anticoagulant is trisodium citrate solution and the second anticoagulant is an anticoagulant other than trisodium citrate solution.

27. The system of claim 20 wherein said first anticoagulant is trisodium citrate solution and said second anticoagulant is selected from the group consisting of ACD-A, ACD-B, and CPD.

28. The system of claim 20 wherein said first anticoagulant is trisodium citrate solution and said second anticoagulant is ACD-A.

29. The system of claim 20 wherein said first anticoagulant is free of dextrose and said second anticoagulant includes dextrose.

30. The system of claim 20 wherein at least said second anticoagulant is free of dextrose, said system further comprising means for separately adding dextrose to said platelets.

31. The system of claim 20 wherein said first anticoagulant source is in direct communication with said whole blood source.

32. The system of claim 20 wherein said first anticoagulant source is located between said whole blood source and said separation chamber.

33. The system of claim 20 wherein said first anticoagulant source comprises a container filled with an anticoagulant.

34. The system of claim 20 wherein said second anticoagulant source comprises a container filled with an anticoagulant.

35. The system of claim 20 wherein said first anticoagulant is selected to improve the sedimentation rate of red blood cells and the second anticoagulant is selected to provide for long-term storage of platelets.

36. In a method for separating blood components from whole blood, wherein anticoagulant is first added to the whole blood, platelet-rich plasma is separated from red cells in the whole blood by allowing the red cells to sediment, anticoagulant is separately added to the platelet-rich plasma, and platelet-rich plasma is then separated into plasma and platelet concentrate, the improvement wherein;
  a) the anticoagulant first added to the whole blood has a pH that is at least about 6.0 and is effective to increase the rate of red cell sedimentation; and
  b) the anticoagulant separately added to the platelet-rich plasma is different from said first added anticoagulant, and includes a nutrient for extended storage of platelets.

37. The method of claim 36 wherein the anticoagulant added to said whole blood has a pH between 6.5 and 7.5.

38. The method of claim 36 wherein the amount of the anticoagulant added to said whole blood comprises 4% or less of the total anticoagulated whole blood volume.

39. The method of claim 36 wherein the amount of the anticoagulant added to said whole blood comprised 3.3% of the total anticoagulated whole blood volume.

40. The method of claim 36 wherein the anticoagulant added to said whole blood is trisodium citrate solution.

41. The method of claim 40 wherein the anticoagulant added to the platelet-rich plasma is selected from the group consisting of ACD-A, ACD-B, and CPD.

42. The method of claim 36 wherein the amount of the anticoagulant added to the platelet-rich plasma comprises between 4% and 10% of the total anticoagulated platelet volume.

43. The method of claim 36 wherein the anticoagulant added to said whole blood has a pH between 6.5 and 7.5 and the amount of said anticoagulant is between approximately 4% and 3.3% of the total anticoagulated whole blood volume and said anticoagulant added to said platelet-rich plasma comprises between 4% and 10% of the total anticoagulated platelet volume.

* * * * *